United States Patent
Abbot et al.

(10) Patent No.: US 11,806,365 B2
(45) Date of Patent: Nov. 7, 2023

(54) MODIFIED T LYMPHOCYTES COMPRISING A CD52 ANTIBODY-INDUCIBLE CASPASE AND METHODS OF APOPTOSIS

(71) Applicant: CELGENE CORPORATION, Summit, NJ (US)

(72) Inventors: Stewart Abbot, San Diego, CA (US); Tianjian Li, Belle Mead, NJ (US); Bitao Liang, Closter, NJ (US)

(73) Assignee: CELGENE CORPORATION, Summit, NJ (US)

( * ) Notice: Subject to any disclaimer, the term of this patent is extended or adjusted under 35 U.S.C. 154(b) by 433 days.

(21) Appl. No.: 17/193,865

(22) Filed: Mar. 5, 2021

(65) Prior Publication Data

US 2021/0299175 A1    Sep. 30, 2021

Related U.S. Application Data

(62) Division of application No. 16/276,581, filed on Feb. 14, 2019, now Pat. No. 10,967,005, which is a division of application No. 14/775,891, filed as application No. PCT/US2014/027039 on Mar. 14, 2014, now Pat. No. 10,238,690.

(60) Provisional application No. 61/794,294, filed on Mar. 15, 2013.

(51) Int. Cl.
| | |
|---|---|
| C12N 5/10 | (2006.01) |
| A61K 35/17 | (2015.01) |
| A61K 38/17 | (2006.01) |
| C07K 14/705 | (2006.01) |
| C07K 16/28 | (2006.01) |
| C12N 5/0783 | (2010.01) |
| C07K 14/725 | (2006.01) |
| C12N 9/64 | (2006.01) |
| A61K 39/395 | (2006.01) |
| A61K 39/00 | (2006.01) |

(52) U.S. Cl.
CPC .......... *A61K 35/17* (2013.01); *A61K 38/1709* (2013.01); *A61K 39/39558* (2013.01); *C07K 14/7051* (2013.01); *C07K 14/70521* (2013.01); *C07K 14/70596* (2013.01); *C07K 16/2803* (2013.01); *C07K 16/2887* (2013.01); *C12N 5/0636* (2013.01); *C12N 9/6475* (2013.01); *A61K 2039/505* (2013.01); *C07K 2317/24* (2013.01); *C07K 2319/03* (2013.01); *C07K 2319/33* (2013.01); *C07K 2319/70* (2013.01); *C12N 2510/00* (2013.01)

(58) Field of Classification Search
None
See application file for complete search history.

(56) References Cited

U.S. PATENT DOCUMENTS

| | | |
|---|---|---|
| 4,554,101 A | 11/1985 | Hopp |
| 4,798,824 A | 1/1989 | Belzer et al. |
| 4,873,192 A | 10/1989 | Kunkel |
| 5,283,173 A | 2/1994 | Fields et al. |
| 5,372,581 A | 12/1994 | Anderson |
| 5,415,665 A | 5/1995 | Hessel et al. |
| 5,468,614 A | 11/1995 | Fields et al. |
| 5,552,267 A | 9/1996 | Stern et al. |
| 5,593,990 A | 1/1997 | D'Amato |
| 5,629,327 A | 5/1997 | D'Amato |
| 5,635,517 A | 6/1997 | Muller et al. |
| 5,665,577 A | 9/1997 | Sodroski et al. |
| 5,677,171 A | 10/1997 | Finn et al. |
| 5,686,281 A | 11/1997 | Roberts |
| 5,698,520 A | 12/1997 | Honjo et al. |
| 5,698,579 A | 12/1997 | Muller |
| 5,712,149 A | 1/1998 | Roberts |
| 5,720,937 A | 2/1998 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,783,404 A | 7/1998 | Koski |
| 5,798,368 A | 8/1998 | Muller et al. |
| 5,827,642 A | 10/1998 | Riddell et al. |
| 5,843,728 A | 12/1998 | Seed et al. |
| 5,858,358 A | 1/1999 | June et al. |
| 5,874,448 A | 2/1999 | Muller et al. |
| 5,877,200 A | 3/1999 | Muller |
| 5,883,223 A | 3/1999 | Gray |
| 5,906,936 A | 5/1999 | Eshhar et al. |

(Continued)

FOREIGN PATENT DOCUMENTS

| | | |
|---|---|---|
| CN | 1764471 A | 4/2006 |
| CN | 101563104 A | 10/2009 |

(Continued)

OTHER PUBLICATIONS

Sholukh et al., Isolation of Monoclonal Antibodies with Predetermined Conformational Epitope Specificity, PLoS One, 7(6):e38943. doi:10.1371/journal.pone.0038943, 2012.*

(Continued)

*Primary Examiner* — Claire Kaufman

(74) *Attorney, Agent, or Firm* — MORRISON & FOERSTER LLP

(57) ABSTRACT

Provided herein are cells, e.g., T cells expressing artificial cell death polypeptides that cause death of a cell, e.g., cells (e.g., T lymphocytes) expressing the cell death polypeptide, when the cell death polypeptide is multimerized or dimerized. Also provided herein is use of such cells, e.g., T lymphocytes, to treat diseases such as cancer.

20 Claims, No Drawings

Specification includes a Sequence Listing.

(56) References Cited

U.S. PATENT DOCUMENTS

| | | | |
|---|---|---|---|
| 5,929,117 A | 7/1999 | Muller et al. | |
| 5,948,893 A | 9/1999 | June et al. | |
| 5,977,318 A | 11/1999 | Linsley et al. | |
| 5,994,136 A | 11/1999 | Naldini et al. | |
| 6,005,079 A | 12/1999 | Casterman et al. | |
| 6,013,516 A | 1/2000 | Verma et al. | |
| 6,040,177 A | 3/2000 | Riddell et al. | |
| 6,071,948 A | 6/2000 | D'Amato | |
| 6,103,521 A | 8/2000 | Capon et al. | |
| 6,120,766 A * | 9/2000 | Hale | A61K 31/57 |
| | | | 530/387.5 |
| 6,165,464 A | 12/2000 | Hudziak et al. | |
| 6,165,782 A | 12/2000 | Naldini et al. | |
| 6,281,230 B1 | 8/2001 | Muller et al. | |
| 6,316,471 B1 | 11/2001 | Muller et al. | |
| 6,319,494 B1 | 11/2001 | Capon et al. | |
| 6,335,349 B1 | 1/2002 | Muller et al. | |
| 6,352,694 B1 | 3/2002 | June et al. | |
| 6,355,699 B1 | 3/2002 | Vyakarnam et al. | |
| 6,387,371 B1 | 5/2002 | Hudziak et al. | |
| 6,399,063 B1 | 6/2002 | Hudziak et al. | |
| 6,410,319 B1 | 6/2002 | Raubitschek et al. | |
| 6,428,953 B1 | 8/2002 | Naldini et al. | |
| 6,476,052 B1 | 11/2002 | Muller et al. | |
| 6,534,055 B1 | 3/2003 | June et al. | |
| 6,682,907 B1 | 1/2004 | Charneau et al. | |
| 6,692,964 B1 | 2/2004 | June et al. | |
| 6,756,036 B2 | 6/2004 | Reiter et al. | |
| 6,790,939 B2 | 9/2004 | Reiter et al. | |
| 6,797,514 B2 | 9/2004 | Berenson et al. | |
| 6,825,326 B2 | 11/2004 | Reiter et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,052,906 B1 | 5/2006 | Lawson et al. | |
| 7,067,318 B2 | 6/2006 | June et al. | |
| 7,070,995 B2 | 7/2006 | Jensen | |
| 7,083,981 B2 | 8/2006 | Naldini et al. | |
| 7,091,353 B2 | 8/2006 | Robarge et al. | |
| 7,144,575 B2 | 12/2006 | June et al. | |
| 7,147,626 B2 | 12/2006 | Goodman et al. | |
| 7,172,869 B2 | 2/2007 | June et al. | |
| 7,175,843 B2 | 2/2007 | June et al. | |
| 7,232,566 B2 | 6/2007 | June et al. | |
| 7,250,299 B1 | 7/2007 | Naldini et al. | |
| 7,264,806 B2 * | 9/2007 | Carr | A61P 9/00 |
| | | | 536/23.53 |
| 7,265,209 B2 | 9/2007 | Jensen | |
| 7,344,715 B2 | 3/2008 | Raison et al. | |
| 7,407,656 B2 | 8/2008 | Reiter et al. | |
| 7,446,179 B2 | 11/2008 | Jensen et al. | |
| 7,446,190 B2 | 11/2008 | Sadelain et al. | |
| 7,446,191 B2 | 11/2008 | Jensen | |
| 7,462,352 B2 | 12/2008 | Hansen et al. | |
| 7,485,296 B2 | 2/2009 | Reiter et al. | |
| 7,514,537 B2 | 4/2009 | Jensen | |
| 7,527,786 B2 | 5/2009 | Reiter et al. | |
| 7,541,442 B2 | 6/2009 | Gudas et al. | |
| 7,556,803 B2 | 7/2009 | Raison et al. | |
| 7,595,379 B2 | 9/2009 | Gudas et al. | |
| 7,655,461 B2 | 2/2010 | Finn et al. | |
| 7,662,378 B2 | 2/2010 | Goldenberg et al. | |
| 7,736,644 B2 | 6/2010 | Weber et al. | |
| 7,741,465 B1 | 6/2010 | Eshhar et al. | |
| 7,902,338 B2 | 3/2011 | Hansen et al. | |
| 7,919,090 B2 | 4/2011 | Goldenberg et al. | |
| 7,951,369 B2 | 5/2011 | Goldenberg et al. | |
| 8,062,636 B2 | 11/2011 | Goldenberg et al. | |
| 8,088,908 B2 | 1/2012 | Sherman et al. | |
| 8,129,124 B2 | 3/2012 | Zhou et al. | |
| 8,147,831 B2 | 4/2012 | Hansen et al. | |
| 8,211,422 B2 | 7/2012 | Eshhar et al. | |
| 8,216,572 B2 | 7/2012 | Goldenberg et al. | |
| 8,287,865 B2 | 10/2012 | Hansen et al. | |
| 8,324,353 B2 | 12/2012 | Jensen et al. | |
| 8,399,645 B2 | 3/2013 | Campana et al. | |
| 8,404,817 B2 | 3/2013 | Sherman et al. | |
| 8,444,973 B2 | 5/2013 | Tedder et al. | |
| 8,465,743 B2 | 6/2013 | Rosenberg et al. | |
| 8,497,118 B2 | 7/2013 | Jensen | |
| 8,530,168 B2 | 9/2013 | Chu et al. | |
| 8,652,470 B2 * | 2/2014 | Hansen | A61P 43/00 |
| | | | 424/133.1 |
| 8,822,647 B2 | 9/2014 | Jensen | |
| 9,469,684 B2 | 10/2016 | Finn et al. | |
| 9,828,361 B2 | 11/2017 | Man et al. | |
| 10,150,816 B2 | 12/2018 | Abbot et al. | |
| 10,238,690 B2 | 3/2019 | Abbot et al. | |
| 2002/0022036 A1 | 2/2002 | He et al. | |
| 2003/0045552 A1 | 3/2003 | Robarge et al. | |
| 2003/0096841 A1 | 5/2003 | Robarge et al. | |
| 2003/0105000 A1 | 6/2003 | Pero et al. | |
| 2003/0147869 A1 | 8/2003 | Riley et al. | |
| 2003/0157713 A1 | 8/2003 | Ohno et al. | |
| 2005/0118185 A1 | 6/2005 | Hombach et al. | |
| 2006/0121005 A1 | 6/2006 | Berenson et al. | |
| 2006/0280732 A1 | 12/2006 | Dudich et al. | |
| 2008/0102027 A1 | 5/2008 | Dunn et al. | |
| 2009/0081172 A1 | 3/2009 | Finn et al. | |
| 2009/0104164 A1 | 4/2009 | Zhang et al. | |
| 2009/0155282 A1 | 6/2009 | Weber et al. | |
| 2009/0156790 A1 | 6/2009 | Weber et al. | |
| 2010/0105136 A1 | 4/2010 | Carter et al. | |
| 2010/0135974 A1 | 6/2010 | Eshhar et al. | |
| 2010/0215651 A1 | 8/2010 | Blein et al. | |
| 2011/0023137 A1 | 1/2011 | Chu et al. | |
| 2011/0033483 A1 | 2/2011 | Thompson et al. | |
| 2011/0229461 A1 | 9/2011 | Tyson et al. | |
| 2011/0286980 A1 | 11/2011 | Brenner | |
| 2012/0034245 A9 | 2/2012 | Thompson et al. | |
| 2012/0093842 A1 | 4/2012 | Eshhar et al. | |
| 2012/0148552 A1 | 6/2012 | Jensen | |
| 2012/0321667 A1 | 12/2012 | Sentman | |
| 2013/0071414 A1 | 3/2013 | Dotti et al. | |
| 2013/0084294 A1 | 4/2013 | Tedder et al. | |
| 2013/0289261 A1 | 10/2013 | Finn et al. | |
| 2013/0323834 A1 | 12/2013 | Brenner | |
| 2014/0023647 A1 | 1/2014 | Slawin et al. | |
| 2014/0087468 A1 | 3/2014 | Spencer et al. | |
| 2014/0162282 A1 | 6/2014 | Schafer et al. | |
| 2014/0286987 A1 | 9/2014 | Spencer et al. | |
| 2014/0294784 A1 | 10/2014 | Waldman et al. | |
| 2014/0322183 A1 | 10/2014 | Milone et al. | |
| 2015/0291562 A1 | 10/2015 | Crew et al. | |
| 2015/0307623 A1 | 10/2015 | Abbot et al. | |
| 2015/0368360 A1 | 12/2015 | Liang et al. | |
| 2016/0030479 A1 | 2/2016 | Abbot et al. | |
| 2016/0151465 A1 | 6/2016 | Slawin et al. | |
| 2016/0264665 A1 | 9/2016 | Lim et al. | |
| 2018/0021378 A1 | 1/2018 | Kang et al. | |
| 2018/0080008 A1 | 3/2018 | Liang et al. | |
| 2018/0273640 A1 | 9/2018 | Liang et al. | |
| 2019/0119399 A1 | 4/2019 | Abbot et al. | |
| 2019/0240304 A1 | 8/2019 | Xu et al. | |

FOREIGN PATENT DOCUMENTS

| | | |
|---|---|---|
| CN | 102031267 | 4/2011 |
| CN | 103483452 A | 1/2014 |
| EP | 404097 B1 | 9/1996 |
| JP | 2003500021 A | 1/2003 |
| JP | 2004113062 A | 4/2004 |
| JP | 2004529636 A | 9/2004 |
| JP | 2005336062 A | 12/2005 |
| JP | 2006518984 A | 8/2006 |
| JP | 2010531638 A | 9/2010 |
| WO | WO 1992008796 A1 | 5/1992 |
| WO | WO 1993001161 A1 | 1/1993 |
| WO | WO 1994004678 A1 | 3/1994 |
| WO | WO 1994025591 A1 | 11/1994 |
| WO | WO 1994028143 A1 | 12/1994 |
| WO | WO 1996005309 A2 | 2/1996 |

(56) References Cited

FOREIGN PATENT DOCUMENTS

| | | |
|---|---|---|
| WO | WO 1996023814 A1 | 8/1996 |
| WO | WO 1998003502 A1 | 1/1998 |
| WO | WO 2000063373 A1 | 10/2000 |
| WO | WO 2002033101 A1 | 4/2002 |
| WO | WO 2002059106 A1 | 8/2002 |
| WO | WO 2002077029 A2 | 10/2002 |
| WO | WO 2002077029 A3 | 10/2002 |
| WO | WO 2002088346 A2 | 11/2002 |
| WO | WO 2002088346 A3 | 11/2002 |
| WO | WO 2003057171 A2 | 7/2003 |
| WO | WO 2003057171 A3 | 7/2003 |
| WO | WO 2004039840 A1 | 5/2004 |
| WO | WO 2004084931 A1 | 10/2004 |
| WO | WO 2006010834 A1 | 2/2006 |
| WO | WO 2007089871 A2 | 8/2007 |
| WO | WO 2007089871 A3 | 8/2007 |
| WO | WO 2008150853 A1 | 12/2008 |
| WO | WO 2008154644 A1 | 12/2008 |
| WO | WO 2010003002 A2 | 1/2010 |
| WO | WO 2010003002 A3 | 1/2010 |
| WO | WO 2010003002 A9 | 1/2010 |
| WO | WO 2010003002 A3 | 9/2010 |
| WO | WO 2010104949 A2 | 9/2010 |
| WO | WO 2010108126 A2 | 9/2010 |
| WO | WO 2010108126 A3 | 9/2010 |
| WO | WO 2011035018 A2 | 3/2011 |
| WO | WO 2011160119 A2 | 12/2011 |
| WO | WO 2011160119 A3 | 12/2011 |
| WO | WO 2011160119 A8 | 12/2011 |
| WO | WO 2012033885 A1 | 3/2012 |
| WO | WO 2012050374 A2 | 4/2012 |
| WO | WO 2012058460 A2 | 5/2012 |
| WO | WO 2012058460 A3 | 5/2012 |
| WO | WO 2012079000 A1 | 6/2012 |
| WO | WO 2012079000 A4 | 6/2012 |
| WO | WO 2012099973 A2 | 7/2012 |
| WO | WO 2012099973 A3 | 7/2012 |
| WO | WO 2012129514 A1 | 9/2012 |
| WO | WO 2012138475 A1 | 10/2012 |
| WO | WO 2012138858 A1 | 10/2012 |
| WO | WO 2013040557 A2 | 3/2013 |
| WO | WO 2013040557 A3 | 3/2013 |
| WO | WO 2013059593 A1 | 4/2013 |
| WO | WO 2013063419 A2 | 5/2013 |
| WO | WO 2013063419 A3 | 5/2013 |
| WO | WO 2013067492 A1 | 5/2013 |
| WO | WO 2013070468 A1 | 5/2013 |
| WO | WO 2013123061 A1 | 8/2013 |
| WO | WO 2013188427 A1 | 12/2013 |
| WO | WO 2014028453 A2 | 2/2014 |
| WO | WO 2014028453 A3 | 2/2014 |
| WO | WO 2014037422 A1 | 3/2014 |
| WO | WO 2014055657 A1 | 4/2014 |
| WO | WO 2014055668 A1 | 4/2014 |
| WO | WO 2014100385 A1 | 6/2014 |
| WO | WO 2014124143 A1 | 8/2014 |
| WO | WO 2014145252 A2 | 9/2014 |
| WO | WO 2014152177 A1 | 9/2014 |
| WO | WO 2014164348 A2 | 10/2014 |
| WO | WO 2014197638 A2 | 12/2014 |
| WO | WO 2015127351 A1 | 8/2015 |
| WO | WO 2016007506 A1 | 1/2016 |
| WO | WO 2016025454 A2 | 2/2016 |
| WO | WO 2016025454 A3 | 2/2016 |
| WO | WO 2016109668 A1 | 7/2016 |
| WO | WO 2018075820 A2 | 4/2018 |
| WO | WO 2018075820 A3 | 4/2018 |
| WO | WO 2018085690 A1 | 5/2018 |
| WO | WO 2020014333 A1 | 1/2020 |

OTHER PUBLICATIONS

Scott et al., Searching for peptide ligands with an eptiope library, Science, 249:386-390, Jul. 27, 1990.*

Abaza et al., 1992, "Effects of amino acid substitutions outside an antigenic site on protein binding to monoclonal antibodies of predetermined specificity obtained by peptide immunization: demonstration with region 94-100 (antigenic site 3) of myoglobin," J Protein Chem., 11(5):433-444.

Ali et al., 2016, "T cells expressing an anti-B-cell maturation antigen chimeric antigen receptor cause remissions of multiple myeloma," Blood, 128(13):1688-1700.

Allikmets et al., 1998, "A human placenta-specific ATP-binding cassette gene (ABCP) on chromosome 4q22 that is involved in multidrug resistance," Cancer Res., 58(23):5337-5339.

Altschul et al., 1997, "Gapped Blast and PSI-Blast: a new generation of protein database search programs," Nucleic Acids Res., 25(17):3389-3402.

Ansel et al., 1999, "In vivo-activated CD4 T cells upregulate CXC chemokine receptor 5 and reprogram their response to lymphoid chemokines," J Exp Med., 190(8):1123-1134.

Anseth et al., 2002, "In situ forming degradable networks and their application in tissue engineering and drug delivery," J Control Release, 78(1-3):199-209.

Asai et al., 2013, "Co-introduced functional CCR2 potentiates in vivo anti-lung cancer functionality mediated by T cells double gene-modified to express WT1-specific T-cell receptor," PLoS One, 8(2):e56820.

Asheuer et al., 2004, "Human CD34+ cells differentiate into microglia and express recombinant therapeutic protein," Proc Natl Acad Sci USA, 101(10):3557-3562.

Avery et al., 2003, "BAFF selectively enhances the survival of plasmablasts generated from human memory B cells," J Clin Invest., 112(2):286-297.

Bakdash et al., 2013, "Harnessing dendritic cells to promote immune tolerance: Opportunities for allergen-specific immunotherapy—Chapter 6: Retinoic acid primes human dendritic cells to induce gut-homing, IL-10 producing regulatory T cells," University of Amsterdam, Ph.D. Thesis, pp. 107-136.

Bakdash et al., 2013, "Intradermal application of vitamin D3 increases migration of CD14+ dermal dendritic cells and promotes the development of Foxp3+ regulatory T cells," Hum. Vaccin. Immunother., 9(2):250-258.

Bakdash, 2013, "Harnessing Dendritic Cells To Promote Immunite Tolerance: Opportunities For Allergen-Specific Immunotherapy," University of Amsterdam, Ph.D. Thesis, retreived from internet: dare.uva.nl/record/1/394938 (169 pages).

Banissi et al., 2009, "Treg depletion with a low-dose metronomic temozolomide regimen in a rat glioma model," Cancer Immunol Immunother, 58(10):1627-1634.

Bedzyk et al., 1990, "Immunological and structural characterization of a high affinity anti-fluorescein single-chain antibody," J Biol Chem., 265(30):18615-18620.

Bell et al., 1999, "The protein CTCF is required for the enhancer blocking activity of vertebrate insulators," Cell, 98(3):387-396.

Bellucci et al., 2005, "Graft-versus-tumor response in patients with multiple myeloma is associated with antibody response to BCMA, a plasma-cell membrane receptor," Blood, 105(10):3945-3950.

Benson et al., 2010, "The PD-1/PD-L1 axis modulates the natural killer cell versus multiple myeloma effect: a therapeutic target for CT-011, a novel monoclonal anti-PD-1 antibody," Blood, 116(13):2286-2294.

Berdeja et al., 2016, "Clinical remissions and limited toxicity in a first-in-human multicenter study of bb2121, a novel anti-BCMA CAR T cell therapy for relapsed/refractory multiple myeloma," European Journal of Cancer, S5, Abstract 14LBA (1 page).

Berdeja et al., 2017, "Durable clinical responses in heavily pretreated patients with relapsed/refractory multiple myeloma: Updated results from a multicenter study of bb2121 anti-BCMA CAR T cell therapy," Blood, 130:740 (7 pages).

Bird et al., 1988, "Single-chain antigen-binding proteins," Science, 242(4877):423-426.

Bissonnette et al., 1994, "Functional Myc-Max heterodimer is required for activation-induced apoptosis in T cell hybridomas", J Exp Med., 180(6):2413-2418.

Bogen et al., 2004, "Recent Trends and Advances in Immunodiagnostics of Solid Tumors," BioDrugs, 18(6):387-398.

(56) References Cited

OTHER PUBLICATIONS

Borden et al., 1987, "Nucleotide sequence of the cDNAs encoding the variable region heavy and light chains of a myeloma protein specific for the terminal nonreducing end of alpha(1--->6)dextran," Proc Natl Acad Sci USA, 84(8):2440-2443.
Burgess et al., 1990, "Possible dissociation of the heparin-binding and mitogenic activities of heparin-binding (acidic fibroblast) growth factor-1 from its receptor-binding activities by site-directed mutagenesis of a single lysine residue," J Cell Biol., 111(5 Pt 1):2129-2138.
Burgess-Beusse et al., 2002, "The insulation of genes from external enhancers and silencing chromatin," Proc Natl Acad Sci USA, 99 Suppl 4(Suppl 4):16433-16437.
Camicia et al., 2015, "Novel drug targets for personalized precision medicine in relapsed/refractory diffuse large B-cell lymphoma: a comprehensive review," Mol. Cancer, 14:207, pp. 1-62.
Cany et al., 2013, "Natural killer cells generated from cord blood hematopoietic progenitor cells efficiently target bone marrow-residing human leukemia cells in NOD/SCID/IL2Rg(null) mice," PLoS One, 8(6):e64384.
Carpenito et al., 2009, "Control of large, established tumor xenografts with genetically retargeted human T cells containing CD28 and CD137 domains," Proc Natl Acad Sci USA, 106(9):3360-3365.
Carpenter et al., 2013, "B-cell maturation antigen is a promising target for adoptive T-cell therapy of multiple myeloma," Clin Cancer Res., 19(8):2048-2060.
Challita et al., 1995, "Multiple modifications in cis elements of the long terminal repeat of retroviral vectors lead to increased expression and decreased DNA methylation in embryonic carcinoma cells," J Virol., 69(2):748-755.
Chaudhary et al., 1990, "A rapid method of cloning functional variable-region antibody genes in *Escherichia coli* as single-chain immunotoxins," Proc Natl Acad Sci USA, 87(3):1066-1070.
Chiu et al., 2007, "Hodgkin lymphoma cells express TACI and BCMA receptors and generate survival and proliferation signals in response to BAFF and April," Blood, 109(2):729-739 (Epub Sep. 7, 2006).
Chmielewski et al., 2012, "T cells that target carcinoembryonic antigen eradicate orthotopic pancreatic carcinomas without inducing autoimmune colitis in mice," Gastroenterology, 143(4):1095-1107.e2.
Chmielewski et al., 2012, "CAR's made it to the pancreas," Oncoimmunology 1(8):1387-1389.
Chothia et al., 1987, "Canonical structures for the hypervariable regions of immunoglobulins," J Mol Biol., 196(4):901-917.
Chothia et al., 1989, "Conformations of immunoglobulin hypervariable regions," Nature, 342(6252):877-883.
Chung et al., 1993, "A 5' element of the chicken beta-globin domain serves as an insulator in human erythroid cells and protects against position effect in *Drosophila*," Cell, 74(3):505-514.
Chung et al., 1997, "Characterization of the chicken beta-globin insulator," Proc Natl Acad Sci USA, 94(2):575-580.
Clever et al., 1995, "RNA secondary structure and binding sites for gag gene products in the 5' packaging signal of human immunodeficiency virus type 1," J Virol., 69(4):2101-2109.
ClinicalTrials.gov Identifier: NCT02658929, "Study of bb2121 in Multiple Myeloma," First Posted: Jan. 20, 2016, Last Update Posted: Aug. 21, 2019 (12 pages).
ClinicalTrials.gov Identifier: NCT03361748, "Efficacy and Safety Study of bb2121 in Subjects With Relapsed and Refractory Multiple Myeloma (KarMMa) (KarMMa)," First Posted: Dec. 5, 2017, Last Update Posted: Sep. 11, 2019 (2 pages).
Cooper et al., 2003, "T-cell clones can be rendered specific for CD19: toward the selective augmentation of the graft-versus-B-lineage leukemia effect," Blood, 101(4):1637-1644 (Epub Oct. 10, 2002).
Craddock et al., 2010, "Enhanced tumor trafficking of GD2 chimeric antigen receptor T cells by expression of the chemokine receptor CCR2b," J Immunother, 33(8):780-788.
Cullen et al., 1989, Regulatory pathways governing HIV-1 replication, Cell, 58(3):423-426.
Cullen, 1991, "Human immunodeficiency virus as a prototypic complex retrovirus," J Virol., 65(3):1053-1056.
Davila et al., 2014, "Chimeric Antigen Receptors for the Adoptive T Cell Therapy of Hematologic Malignancies," Int J Hematol., 99(4):361-371 (Epub 2013).
De Felipe et al., 2004, "Targeting of proteins derived from self-processing polyproteins containing multiple signal sequences," Traffic, 5(8):616-626.
Desjarlais et al., 1993, "Use of a zinc-finger consensus sequence framework and specificity rules to design specific DNA binding proteins," Proc Natl Acad Sci USA, 90(6):2256-2260.
Desjarlais et al., 1994, "Length-encoded multiplex binding site determination: application to zinc finger proteins," Proc Natl Acad Sci USA, 91(23):11099-11103.
Di Stasi et al., 2009, "T lymphocytes coexpressing CCR4 and a chimeric antigen receptor targeting CD30 have improved homing and antitumor activity in a Hodgkin tumor model," Blood, 113(25):6392-6402.
Di Stasi et al., 2011, "Inducible apoptosis as a safety switch for adoptive cell therapy", N. Engl. J. Med., 365(18):1673-1683.
Dobson et al., 2015, "The human transmembrane proteome," Biol. Direct., 10:31 (18 pages).
Donnelly et al., 2001, "The 'cleavage' activities of foot-and-mouth disease virus 2A site-directed mutants and naturally occurring '2A-like' sequences," J Gen Virol., 82(Pt 5):1027-1041.
Duong et al., 2011, "Enhancing the specificity of T-cell cultures for adoptive immunotherapy of cancer," Immunotherapy, 3(1):33-48.
Edwards et al., 2003, "The remarkable flexibility of the human antibody repertoire; isolation of over one thousand different antibodies to a single protein, BLyS," J Mol Biol., 334(1):103-118.
Ercolini et al., 2005, "Recruitment of latent pools of high-avidity CD8(+) T cells to the antitumor immune response," J Exp Med., 201(10):1591-1602.
European Extended Search Report and Search Opinion dated Jun. 8, 2016 of European Patent Application No. 13865885.1 (8 pages).
European Search Report and Search Opinion dated Mar. 1, 2019 of European Patent Application No. 18195425.6 (7 pages).
Fedorov et al., 2013, "PD-1- and CTLA-4-based inhibitory chimeric antigen receptors (iCARs) divert off-target immunotherapy responses," Sci. Transl. Med. 5(215):215ra172 (13 pages).
Ferlazzo et al., 2004, "The abundant NK cells in human secondary lymphoid tissues require activation to express killer cell Ig-like receptors and become cytolytic," J Immunol., 172(3):1455-1462.
Fire et al., 1998, "Potent and specific genetic interference by double-stranded RNA in Caenorhabditis elegans," Nature, 391(6669):806-811.
Fitzer-Attas et al., 1998, "Harnessing Syk family tyrosine kinases as signaling domains for chimeric single chain of the variable domain receptors: optimal design for T cell activation," J. Immunol., 160(1):145-154.
Friedman et al., 2018, "Effective Targeting of Multiple B-Cell Maturation Antigen-Expressing Hematological Malignances by Anti-B-Cell Maturation Antigen Chimeric Antigen Receptor T Cells," Hum Gene Ther., 29(5):585-601.
Gandhi et al., 2014, "Immunomodulatory agents lenalidomide and pomalidomide co-stimulate T cells by inducing degradation of T cell repressors Ikaros and Aiolos via modulation of the E3 ubiquitin ligase complex CRL4$^{CRBN}$," Br. J. Haematol., 164(6):811-821. [First published online Dec. 13, 2013].
GenBank Accession No. AA107160.1, "ml57d12.r1 Stratagene mouse testis (#937308) Mus musculus CDNA clone Image:516119 5' similar to TR:G600529 G600529 NADH Ubiquinone Oxidoreductase Subunit, mRNA sequence" (Feb. 3, 1997).
GenBank Accession No. BC107159.1, "*Homo sapiens* chemokine (C-C motif) receptor 8, mRNA (cDNA clone MGC:129973 Image:40032938), complete cds" (Oct. 4, 2006).
GenBank Accession No. NM_000885.4, "*Homo sapiens* integrin, alpha 4 (antigen CD49D, alpha 4 subunit of VLA-4 receptor) (ITGA4), mRNA" (Mar. 15, 2015).
GenBank Accession No. NM_000889.2, "*Homo sapiens* integrin subunit beta 7 (ITGB7), transcript variant 1, mRNA" (Jun. 30, 2018).

(56) References Cited

OTHER PUBLICATIONS

GenBank Accession No. NM_001008540.1, "*Homo sapiens* C-X-C motif chemokine receptor 4 (CXCR4), transcript variant 1, mRNA" (Dec. 21, 2016).
GenBank Accession No. NM_001206609.1, "*Homo sapiens* selectin P ligand (SELPLG), transcript variant 1, mRNA" (Oct. 13, 2018).
GenBank Accession No. NM_001256369.1, "*Homo sapiens* C-C motif chemokine receptor 9 (CCR9), transcript variant C, mRNA" (Jun. 3, 2018).
GenBank Accession No. NM_001301714.1, "*Homo sapiens* C-C motif chemokine receptor 7 (CCR7), transcript variant 2, mRNA" (Apr. 2, 2019).
GenBank Accession No. NM_001301716.1, "*Homo sapiens* C-C motif chemokine receptor 7 (CCR7), transcript variant 3, mRNA" (Apr. 2, 2019).
GenBank Accession No. NM_001301717.1, "*Homo sapiens* C-C motif chemokine receptor 7 (CCR7), transcript variant 4, mRNA" (Apr. 2, 2019).
GenBank Accession No. NM_001301718.1, "*Homo sapiens* C-C motif chemokine receptor 7 (CCR7), transcript variant 5, mRNA" (Apr. 2, 2019).
GenBank Accession No. NM_001716.4, "*Homo sapiens* C-X-C motif chemokine receptor 5 (CXCR5), transcript variant 1, mRNA" (Apr. 9, 2019).
GenBank Accession No. NM_001838.3, "*Homo sapiens* C-C motif chemokine receptor 7 (CCR7), transcript variant 1, mRNA" (Jun. 3, 2018).
GenBank Accession No. NM_002253.2, "*Homo sapiens* kinase insert domain receptor (KDR), mRNA" (Dec. 18, 2017).
GenBank Accession No. NM_003006.4, "*Homo sapiens* selectin P ligand (SELPLG), transcript variant 2, mRNA" (Feb. 23, 2019).
GenBank Accession No. NM_003467.2, "*Homo sapiens* C-X-C motif chemokine receptor 4 (CXCR4), transcript variant 2, mRNA" (Apr. 23, 2019).
GenBank Accession No. NM_005201.3, "*Homo sapiens* C-C motif chemokine receptor 8 (CCR8), mRNA" (Feb. 18, 2019).
GenBank Accession No. NM_005508.4, "*Homo sapiens* C-C motif chemokine receptor 4 (CCR4), mRNA" (Mar. 25, 2019).
GenBank Accession No. NM_016602.2, "*Homo sapiens* C-C motif chemokine receptor 10 (CCR10), mRNA" (Jun. 24, 2018).
GenBank Accession No. NM_031200.2, "*Homo sapiens* C-C motif chemokine receptor 9 (CCR9), transcript variant A, mRNA" (Jun. 3, 2018).
GenBank Accession No. NM_032966.2, "*Homo sapiens* C-X-C motif chemokine receptor 5 (CXCR5), transcript variant 2, mRNA" (Apr. 9, 2019).
GenBank Accession No. NP_000876.3, "integrin alpha-4 isoform 1 preproprotein [*Homo sapiens*]" (Feb. 10, 2019).
GenBank Accession No. NP_000880.1, "integrin beta-7 precursor [*Homo sapiens*]" (Mar. 25, 2019).
GenBank Accession No. NP_001008540.1, "C-X-C chemokine receptor type 4 isoform a [*Homo sapiens*]" (Apr. 23, 2019).
GenBank Accession No. NP_001193538.1, "P-selectin glycoprotein ligand 1 isoform 1 precursor [*Homo sapiens*]" (Oct. 13, 2018).
GenBank Accession No. NP_001243298.1, "C-C chemokine receptor type 9 isoform B [*Homo sapiens*]" (Jun. 3, 2018).
GenBank Accession No. NP_001288643.1, "C-C chemokine receptor type 7 isoform b [*Homo sapiens*]" (Apr. 2, 2019).
GenBank Accession No. NP_001288645.1, "C-C chemokine receptor type 7 isoform c precursor [*Homo sapiens*]" (Apr. 2, 2019).
GenBank Accession No. NP_001288646.1, "C-C chemokine receptor type 7 isoform c [*Homo sapiens*]" (Apr. 2, 2019).
GenBank Accession No. NP_001288647.1, "C-C chemokine receptor type 7 isoform c [*Homo sapiens*]" (Apr. 2, 2019).
GenBank Accession No. NP_001829.1, "C-C chemokine receptor type 7 isoform a precursor [*Homo sapiens*]" (Apr. 2, 2019).
GenBank Accession No. NP_002244.1, "vascular endothelial growth factor receptor 2 precursor [*Homo sapiens*]" (Apr. 20, 2019).
GenBank Accession No. NP_002997.2, "P-selectin glycoprotein ligand 1 isoform 2 precursor [*Homo sapiens*]" (Feb. 23, 2019).
GenBank Accession No. NP_003458.1, "C-X-C chemokine receptor type 4 isoform b [*Homo sapiens*]" (Apr. 23, 2019).
GenBank Accession No. NP_005192.1, "C-C chemokine receptor type 8 [*Homo sapiens*]" (Feb. 18, 2019).
GenBank Accession No. NP_057686.2, "C-C chemokine receptor type 10 [*Homo sapiens*]" (Dec. 29, 2018).
GenBank Accession No. NP_112477.1, "C-C chemokine receptor type 9 isoform A [*Homo sapiens*]" (Feb. 10, 2019).
GenBank Accession No. NP_116743.1, "C-X-C chemokine receptor type 5 isoform 2 [*Homo sapiens*]" (Apr. 9, 2019).
GenBank Accession No. P46092.3, "RecName: Full=C-C chemokine receptor type 10; Short=C-C CKR-10; Short=CC-CKR-10; Short=CCR-10; AltName: Full=G-protein coupled receptor 2" (Apr. 10, 2019).
GenBank Accession No. P51679.1, "RecName: Full=C-C chemokine receptor type 4; Short=C-C CKR-4; Short=CC-CKR-4; Short=CCR-4; Short=CCR4; AltName: Full=K5-5; AltName: CD antigen=CD 194" (Apr. 10, 2019).
GenBank Gene ID: 10320, IKZF1 Ikaros family zinc finger 1 [*Homo sapiens* (human)], updated Aug. 6, 2019, retreived from https://www.ncbi.nlm.nih.gov/gene/10320 on Aug. 9, 2019.
GenBank Gene ID: 22806, IKZF3 Ikaros family zinc finger 3 [*Homo sapiens* (human)], updated Aug. 4, 2019, retreived from https://www.ncbi.nlm.nih.gov/gene/22806 on Aug. 9, 2019.
GenBank Gene ID: 51185, CRBN cereblon [*Homo sapiens* (human)], updated Jun. 17, 2019, retreived from https://www.ncbi.nlm.nih.gov/gene/51185 on Aug. 9, 2019.
Ghermezi et al., 2017, "Serum B-cell maturation antigen: a novel biomarker to predict outcomes for multiple myeloma patients," Haematologica, 102(4):785-795.
Gleason et al., 2012, "Bispecific and trispecific killer cell engagers directly activate human NK cells through CD16 signaling and induce cytotoxicity and cytokine production," Mol Cancer Ther., 11(12):2674-2684.
Gleason et al., 2014, "CD16×CD33 bispecific killer cell engager (BiKE) activates NK cells against primary MDS and MDSC CD33+ targets," Blood, 123(19):3016-3026.
Haanen eta l., 1999, "Selective expansion of cross-reactive CD8(+) memory T cells by viral variants," J Exp Med., 90(9):1319-1328.
Han et al., 2013, "Chimeric antigen receptor-engineered T cells for cancer immunotherapy: progress and challenges," J Hematol Oncol., 6:47 (7 pages).
Harper et al., 1991, "CTLA-4 and CD28 activated lymphocyte molecules are closely related in both mouse and human as to sequence, message expression, gene structure, and chromosomal location," J. Immunol., 147(3):1037-1044.
Hegde et al., 2011, "Abstract 913: Targeting tumor heterogeneity in glioblastoma: bispecific T cells exhibit enhanced effector functions and offset antigen loss escape variants," American Society of Cell and Gene Therapy, 19(7):1388 (2 pages).
Holash et al., 2002, "VEGF-Trap: a VEGF blocker with potent antitumor effects," Proc. Natl. Acad. Sci. USA 99(17):11393-11398.
Holliger et al., 1993, ""Diabodies": small bivalent and bispecific antibody fragments," Proc Natl Acad Sci USA, 90(14):6444-6448.
Hoyos et al., 2012, "Genetic modification of human T lymphocytes for the treatment of hematologic malignancies," Haematologica, 97(11):1622-1631.
Huang et al., 2008, "Oral supplementation of lutein/zeaxanthin and omega-3 long chain polyunsaturated fatty acids in persons aged 60 years or older, with or without AMD," Invest Ophthalmol Vis Sci., 49(9):3864-3869.
Hudson et al., 2003, "Engineered antibodies," Nat Med., 9(1):129-134.
Hyrup et al., 1996, "Peptide nucleic acids (PNA): synthesis, properties and potential applications," Bioorg Med Chem., 4(1):5-23.
Ibragimova et al., 1999, "Stability of the beta-sheet of the WW domain: A molecular dynamics simulation study," Biophys. J., 77(4):2191-2198.
International Search Report and Written Opinion of International Patent Application No. PCT/US2013/076486 (Pub No. WO 2014100385) dated Mar. 6, 2014 (9 pages).

(56) References Cited

OTHER PUBLICATIONS

International Search Report and Written Opinion of International Patent Application No. PCT/US2014/015113 (Pub No. WO 2014124143) dated Jul. 9, 2014 (14 pages).
International Search Report and Written Opinion of International Patent Application No. PCT/US2015/044611 (Pub No. WO 2016025454) dated Jan. 21, 2016 (17 pages).
International Search Report and Written Opinion of International Patent Application No. PCT/US2017/057474 (Pub No. WO 2018075820) dated Jan. 22, 2018 (19 pages).
International Search Report and Written Opinion of International Patent Application No. PCT/US2019/041165 (Pub. No. WO 2020014333) dated Oct. 15, 2019 (16 pages).
International Search Report and Written Opinion of International Patent Application PCT/US2015/068069 (Pub No. WO 2016109668) dated Mar. 31, 2016 (17 pages).
International Search Report of International Patent Application No. PCT/US2014/027039 (Pub No. WO 2014152177) dated Jul. 7, 2014 (4 pages).
Introna et al., 2000, "Genetic modification of human T cells with CD20: a strategy to purify and lyse transduced cells with anti-CD20 antibodies," Hum. Gene Ther., 11(4):611-620.
Irion et al., 2007, "Identification and targeting of the ROSA26 locus in human embryonic stem cells," Nat Biotechnol, 25(12):1477-1482.
Jackson et al., 1995, "Internal initiation of translation in eukaryotes: the picornavirus paradigm and beyond," RNA, 1(10):985-1000.
Jena et al., 2010, "Redirecting T-cell specificity by introducing a tumor-specific chimeric antigen receptor," Blood, 116(7):1035-1044.
Kalled, 2005, "The role of BAFF in immune function and implications for autoimmunity" Immunol Rev., 204:43-54.
Kametaka et al., 2003, "Reduction of CTLL-2 cytotoxicity by induction of apoptosis with a Fas-estrogen receptor chimera", Cancer Sci., 94(7):639-643.
Kay, 1997, "Adenoviral vectors for hepatic gene transfer in animals," Chest, 111(6 Suppl):138S-142S.
Kershaw et al., 2002, "Redirecting migration of T cells to chemokine secreted from tumors by genetic modification with CXCR2," Hum. Gene Ther., 13(16):1971-1980.
Kershaw et al., 2013, "Gene-engineered T Cells for Cancer Therapy," Nat Rev Cancer, 13(8):525-541.
Kim et al., 1996, "Hybrid restriction enzymes: zinc finger fusions to Fok I cleavage domain," Proc Natl Acad Sci USA, 93(3):1156-1160.
Kloss et al., 2013, "Combinatorial antigen recognition with balanced signaling promotes selective tumor eradication by engineered T cells," Nat. Biotechnol., 31(1):71-75.
Kocoglu et al., 2016, "The Role of Immunotherapy in Multiple Myeloma," Pharmaceuticals (Basel), 9(1) (13 pages).
Koehler et al., 2012, "Engineered T cells for the adoptive therapy of B-cell chronic lymphocytic leukaemia," Advances in Hematology, vol. 2012, Article ID 595060 (13 pages).
Kozak, 1986, "Point mutations define a sequence flanking the AUG initiator codon that modulates translation by eukaryotic ribosomes," Cell, 44(2):283-292.
Kozak, 1987, "An analysis of 5'-noncoding sequences from 699 vertebrate messenger RNAs," Nucleic Acids Res., 15(20):8125-8148.
Kunkel, 1985, "Rapid and efficient site-specific mutagenesis without phenotypic selection," Proc Natl Acad Sci USA, 82(2):488-492.
Laabi et al., 1992, "A new gene, BCM, on chromosome 16 is fused to the interleukin 2 gene by a t(4;16)(q26;p13) translocation in a malignant T cell lymphoma," EMBO J., 11(11):3897-3904.
Laabi et al., 1994, "The BCMA gene, preferentially expressed during B lymphoid maturation, is bidirectionally transcribed," Nucleic Acids Res., 22(7):1147-1154.
Landau et al., 1992, "Packaging system for rapid production of murine leukemia virus vectors with variable tropism," J Virol., 66(8):5110-5113.
Lázár-Molnár et al., 2008, "Crystal structure of the complex between programmed death-1 (PD-1) and its ligand PD-L2," Proc. Natl. Acad. Sci. USA, 105(30):10483-10488.
Lee et al., 2000, "Remission in models of type 1 diabetes by gene therapy using a single-chain insulin analogue," Nature, 408(6811):483-488 and Retraction published Apr. 2, 2009.
Lehmann et al., 2012, "Ex vivo generated natural killer cells acquire typical natural killer receptors and display a cytotoxic gene expression profile similar to peripheral blood natural killer cells," Stem Cells Dev., 21(16):2926-2938.
Lin et al., 1999, "RNA interference. Policing rogue genes," Nature, 402(6758):128-129.
Litterman et al., 2013, "Profound impairment of adaptive immune responses by alkylating chemotherapy," J Immunol., 190(12):6259-6268.
Litwin et al., 1993, "Specificity of HLA class I antigen recognition by human NK clones: evidence for clonal heterogeneity, protection by self and non-self alleles, and influence of the target cell type," J Exp Med., 178(4):1321-1336.
Liu et al., 1995, "HnRNP L binds a cis-acting RNA sequence element that enables intron-dependent gene expression," Genes Dev., 9(14):1766-1780.
Liu et al., 1997, "Design of polydactyl zinc-finger proteins for unique addressing within complex genomes," Proc Natl Acad Sci USA, 94(11):5525-5530.
Liu et al., 2009, "Targeting the phosphoinositide 3-kinase pathway in cancer," Nat Rev Drug Discov., 8(8):627-644.
Liu et al., 2011, "BAFF inhibition: a new class of drugs for the treatment of autoimmunity," Exp Cell Res., 317(9):1270-1277.
Lloyd et al., 2009, "Modelling the human immune response: performance of a 1011 human antibody repertoire against a broad panel of therapeutically relevant antigens," Protein Eng Des Sel., 22(3):159-168, Epub Oct. 29, 2008.
Lupton et al., 1991, "Dominant positive and negative selection using a hygromycin phosphotransferase-thymidine kinase fusion gene," Mol Cell Biol., 11(6):3374-3378.
Mackay et al., 2003, "BAFF and April: a tutorial on B cell survival," Annu Rev Immunol., 21:231-264.
Maher, 2012, "Immunotherapy of malignant disease using chimeric antigen receptor engrafted T cells", ISRN Oncol., 2012:278093 (23 pages).
Majzner et al., 2018, "Tumor Antigen Escape from CAR T-cell Therapy," Cancer Discov., 8(10):1219-1226.
Maki et al., 2008, "MEK1/2 induces STAT5-mediated germline transcription of the TCRgamma locus in response to IL-7R signaling," J. Immunol. 181(1):494-502.
Mariuzza et al., 1987, "The structural basis of antigen-antibody recognition," Annu Rev Biophys Biophys Chem., 16:139-159.
Matsushita et al., 2005, "The role of BAFF in autoimmune diseases," Jpn. J. Clin. Immunol., 28(5):333-342 (in Japanese with English abstract).
Meuer et al., 1984, "An alternative pathway of T-cell activation: a functional role for the 50 kd T11 sheep erythrocyte receptor protein," Cell, 36(4):897-906.
Milone et al., 2009, "Chimeric receptors containing CD137 signal transduction domains mediate enhanced survival of T cells and increased antileukemic efficacy in vivo," Mol Ther., 17(8):1453-1464.
Montaldo et al., 2012, "Human NK cells at early stages of differentiation produce CXCL8 and express CD161 molecule that functions as an activating receptor," Blood, 119(17):3987-3996.
Moon et al., 2011, "Expression of a functional CCR2 receptor enhances tumor localization and tumor eradication by retargeted human T cells expressing a mesothelin-specific chimeric antibody receptor," Clin Cancer Res., 17(14):4719-4730.
Mora et al., 2008, "Vitamin effects on the immune system: vitamins A and D take centre stage," Nat Rev Immunol., 8(9):685-698.
Moreaux et al., 2004, "BAFF and April protect myeloma cells from apoptosis induced by interleukin 6 deprivation and dexamethasone," Blood, 103(8):3148-3157 (Epub Dec. 4, 2003).
Morgan et al., 2010, "Case report of a serious adverse event following the administration of T cells transduced with a chimeric antigen receptor recognizing ERBB2," Mol Ther., 18(4):843-851.

(56) References Cited

OTHER PUBLICATIONS

Mullen et al., 1992, "Transfer of the bacterial gene for cytosine deaminase to mammalian cells confers lethal sensitivity to 5-fluorocytosine: a negative selection system," Proc Natl Acad Sci USA, 89(1):33-37.
Munshi et al., 2020, "Idecabtagene vicleucel (ide-cel; bb2121), a BCMA-targeted CAR T-cell therapy, in patients with relapsed and refractory multiple myeloma (RRMM): Initial KarMMa results," Journal of Clinical Oncology, 38(15):Abstract 8503.
Nakamura et al., 1986, "Purification and Characterization of a Growth Factor From Rat Platelets for Mature Parenchymal Hepatocytes in Primary Cultures," Proc Natl Acad Sci USA, 83(17):6489-6493.
Neri et al., 2007, "Neutralizing B-cell activating factor antibody improves survival and inhibits osteoclastogenesis in a severe combined immunodeficient human multiple myeloma model," Clin Cancer Res., 13(19):5903-5909.
Ng et al., 2004, "B cell-activating factor belonging to the TNF family (BAFF)-R is the principal BAFF receptor facilitating BAFF costimulation of circulating T and B cells," J Immunol., 173(2):807-817.
Novak et al., 2004, "Expression of BCMA, TACI, and BAFF-R in multiple myeloma: a mechanism for growth and survival," Blood, 103(2):689-694.
O'Connor et al., 2004, "BCMA is essential for the survival of long-lived bone marrow plasma cells," J Exp Med., 199(1):91-97.
Okutsu et al., 2014, "Cortisol is not the primary mediator for augmented CXCR4 expression on natural killer cells after acute exercise," J Appl Physiol, 117(3):199-204.
Orlandi et al., 1989, "Cloning immunoglobulin variable domains for expression by the polymerase chain reaction," Proc Natl Acad Sci USA, 86(10):3833-3837.
Pappa et al., 2014, "Prognostic impact of angiopoietin-2 in multiple myeloma," J Cancer Res Clin Oncol., 140(10):1801-1805.
Patel et al., 1999, "Impact of chimeric immune receptor extracellular protein domains on T cell function" Gene Ther., 6(3):412-419.
Pegram et al., 2014, "CD28z CARs and armored CARs," Cancer J., 20(2):127-133.
Perica et al., 2018, "Building a CAR Garage: Preparing for the Delivery of Commercial CAR T Cell Products at Memorial Sloan Kettering Cancer Center," Biol Blood Marrow Transplant, 24(6):1135-1141.
Pomerantz et al., 1995, "Structure-based design of transcription factors," Science, 267(5194):93-96.
Raje et al., 2019, "Anti-BCMA CAR T-Cell Therapy bb2121 in Relapsed or Refractory Multiple Myeloma," N Engl J Med., 380(18):1726-1737.
Reiners et al., 2013, "Rescue of impaired NK cell activity in hodgkin lymphoma with bispecific antibodies in vitro and in patients," Mol Ther., 21(4):895-903.
Reiss et al., 2001, "CC chemokine receptor (CCR)4 and the CCR10 ligand cutaneous T cell-attracting chemokine (CTACK) in lymphocyte trafficking to inflamed skin," J Exp Med., 194(10):1541-1547.
Riet, 2010, "Erhöhung der Antigen-Selektivität von T-Zellen durch Koexpression chimärer Antigen-Rezeptoren unterschiedlicher Spezifität," Ph.D. thesis, Dissertation Universitat zu Koln, retrieved from http://kups.ub.uni-koeln.de/3261, in German with English abstract only (204 pages).
Riet, 2010, "Increase of the antigen selectivity of T-cells by Koexpression of chimeric antigen receptors of divergent specificity," Ph.D. thesis, Dissertation Universitat zu Koln, machine English translation (204 pages).
Rudikoff et al., 1982, "Single amino acid substitution altering antigen-binding specificity," Proc Natl Acad Sci USA, 79(6):1979-1983.
Sadelain et al., 2013, "The basic principles of chimeric antigen receptor design," Cancer Discov., 3(4):388-398.
Sanchez et al., 2012, "Serum B-cell maturation antigen is elevated in multiple myeloma and correlates with disease status and survival," Br J Haematol, 158(6):727-738.

Schiemann et al., 2001, "An essential role for BAFF in the normal development of B cells through a BCMA-independent pathway," Science, 293(5537):2111-2114.
Shah et al., 2018, "Initial Results from a Phase 1 Clinical Study of bb21217, a Next-Generation Anti Bcma CAR T Therapy," Blood, 132:488 (6 pages).
Shah et al., 2020, "B-cell maturation antigen (BCMA) in multiple myeloma: rationale for targeting and current therapeutic approaches," Leukemia, 34(4):985-1005.
Sharp, 1999, "RNAi and double-strand RNA," Genes Dev., 13(2):139-141.
Shi et al., 2014, "Chimeric antigen receptor for adoptive immunotherapy of cancer: latest research and future prospects," Mol. Cancer, 13(219) (8 pages).
Shimabukuro-Vornhagen et al., 2018, "Cytokine release syndrome," J Immunother Cancer, 6(1):56 (14 pages).
Shin et al., 2012 "Positive conversion of negative signaling of CTLA4 potentiates antitumor efficacy of adoptive T-cell therapy in murine tumor models," Blood, 119(24):5678-5687.
Shiratori et al., 1999, "Strategy of liver-directed gene therapy: present status and future prospects," Liver, 19(4):265-274.
Sigmundsdottir et al., 2007, "DCs metabolize sunlight-induced vitamin D3 to 'program' T cell attraction to the epidermal chemokine CCL27," Nat Immunol., 8(3):285-293.
Singer et al., 2010, "Effective elimination of acute myeloid leukemic cells by recombinant bispecific antibody derivatives directed against CD33 and CD16," J Immunother., 33(6):599-608.
Somanchi et al., 2012, "Engineering lymph node homing of ex vivo-expanded human natural killer cells via trogocytosis of the chemokine receptor CCR7," Blood, 119(22):5164-5172.
Soneoka et al., 1995, "A transient three-plasmid expression system for the production of high titer retroviral vectors," Nucleic Acids Res., 23(4):628-633.
Song et al., 2013, "Chimeric NKG2D CAR-expressing T cell-mediated attack of human ovarian cancer is enhanced by histone deacetylase inhibition," Hum Gene Ther., 24(3):295-305.
Sonneveld et al., 2016, "Treatment of relapsed and refractory multiple myeloma," Haematologica, 101(4):396-406 and Errata Corrige published 101(8):995.
Southard et al., 1990, "Important components of the UW solution," Transplantation, 49(2):251-257.
Straathof et al., 2005, "An inducible caspase 9 safety switch for T-cell therapy," Blood, 105(11):4247-4254.
Summerton et al., 1997, "Morpholino antisense oligomers: design, preparation, and properties," Antisense Nucleic Acid Drug Dev., 7(3):187-195.
Supplemental European Search Report of European Patent Application No. 14770151.0 completed Aug. 11, 2016 (1 page).
Szymczak et al., 2004, "Correction of multi-gene deficiency in vivo using a single 'self-cleaving' 2A peptide-based retroviral vector," Nat Biotechnol, 22(5):589-594 with Errata, Corrigenda and Addenda published Jun. 1, 2004 and Dec. 1, 2004.
Terpos et al., 2012, "Circulating angiopoietin-1 to angiopoietin-2 ratio is an independent prognostic factor for survival in newly diagnosed patients with multiple myeloma who received therapy with novel antimyeloma agents," Int J Cancer, 130(3):735-742.
Tey et al., 2007, "Inducible caspase 9 suicide gene to improve the safety of allodepleted T cells after haploidentical stem cell transplantation," Biol. Blood Marrow Transplant., 13(8):913-924.
The Human Protein Atlas, Gene Name: CLEC12A, C-type lectin domain family 12 member A, retrieved from internet: http://www.proteinatlas.org/ENSG00000172322-CLEC12A/pathology, on Jan. 28, 2020 (2 pages).
Thomis et al., 2001, "A Fas-based suicide switch in human T cells for the treatment of graft-versus-host disease," Blood, 97(5):1249-1257.
Thompson et al., 2000, "BAFF binds to the tumor necrosis factor receptor-like molecule B cell maturation antigen and is important for maintaining the peripheral B cell population," J Exp Med., 192(1):129-135.
Thule eta l., 2000, "Regulated hepatic insulin gene therapy of STZ-diabetic rats," Gene Ther., 7(20):1744-1752.

(56) References Cited

OTHER PUBLICATIONS

Tsuji et al., 2003, "Concurrent induction of T-cell activation and apoptosis of osteosarcoma cells by adenovirus-mediated B7-1/Fas chimeric gene transfer", Cancer Gene Ther., 10(9):717-725.
UniProtKB—Q03267 (IKZF1_Mouse), DNA-binding protein Ikaros, retrieved from https://www.uniprot.org/uniprot/Q03267-1 on Aug. 9, 2019, Integrated into UniProtKB/Swiss-Prot on Oct. 1, 1993, Last sequence update Dec. 15, 1998.
UniProtKB—Q96SW2 (CRBN_Human), Protein cereblon, retrieved from https://www.uniprot.org/uniprot/Q96SW2 on Aug. 9, 2019, Integrated into UniProtKB/Swiss-Prot on Aug. 30, 2005, Last sequence update Dec. 1, 2001.
UniProtKB—Q9UKT9 (IKZF3_Human), Zinc finger protein Aiolos, retrieved from https://www.uniprot.org/uniprot/Q9UKT9 on Aug. 9, 2019, Integrated into UniProtKB/Swiss-Prot on Sep. 19, 2002, Last sequence update Nov. 4, 2008.
Vallera et al., 2013, "Heterodimeric bispecific single-chain variable-fragment antibodies against EpCAM and CD16 induce effective antibody-dependent cellular cytotoxicity against human carcinoma cells," Cancer Biother Radiopharm., 28(4):274-282.
Van Der Stegen et al., 2015, "The pharmacology of second-generation chimeric antigen receptors," Nat Rev Drug Discov., 14(7):499-509.
Wang et al., 2003, "Synthesis and characterization of a novel degradable phosphate-containing hydrogel," Biomaterials, 24(22):3969-3980.
Wang et al., 2016, "Clinical manufacturing of CAR T cells: foundation of a promising therapy," Mol Ther Oncolytics, 3:16015 (7 pages).
Ware et al., 1976, "Reanalysis of some baboon descent data," Biometrics, 32(2):459-463.
Wiernik et al., 2013, "Targeting natural killer cells to acute myeloid leukemia in vitro with a CD16×33 bispecific killer cell engager and ADAM17 inhibition," Clin Cancer Res., 19(14):3844-3855.
Wigler et al., 1977, "Transfer of purified herpes virus thymidine kinase gene to cultured mouse cells," Cell, 11(1):223-232.
Wikipedia, B-cell maturation antigen (BCMA) definition/description, 2017.
Wilkie et al., 2010, "Selective expansion of chimeric antigen receptor-targeted T-cells with potent effector function using interleukin-4," J Biol Chem., 285(33):25538-25544.
Wilkie et al., 2012, "Dual targeting of ErbB2 and MUC1 in breast cancer using chimeric antigen receptors engineered to provide complementary signaling," J Clin Immunol. 32(5):1059-1070.
Written Opinion of International Patent Application No. PCT/US2014/027039 (Pub No. WO2014152177) dated Jul. 7, 2014 (14 pages).
Wu et al., 1970, "An analysis of the sequences of the variable regions of Bence Jones proteins and myeloma light chains and their implications for antibody complementarity," J Exp Med., 132(2):211-250.
Wu et al., 2015, "Remote control of therapeutic T cells through a small molecule-gated chimeric receptor," Science, 350(6258):aab4077 (11 pages).
Xu et al., 2001, "B-cell maturation protein, which binds the tumor necrosis factor family members BAFF and April, is dispensable for humoral immune responses," Mol Cell Biol., 21(12):4067-4074.
Yang et al., 1986, "A common pathway for T lymphocyte activation involving both the CD3-Ti complex and CD2 sheep erythrocyte receptor determinants," J Immunol, 137(4):1097-1100.
Yoshie, 2013, "Chemokine receptors as therapeutic targets," Jpn. J. Clini. Immunol., 36(4):189-196 (in Japanese with English Abstract).
Yssel et al., 1984, "Serum-free medium for generation and propagation of functional human cytotoxic and helper T cell clones," J Immunol Methods., 72(1):219-227.
Zamore et al., 2000, "RNAi: double-stranded RNA directs the ATP-dependent cleavage of mRNA at 21 to 23 nucleotide intervals," Cell, 101(1):25-33.
Zennou et al., 2000, "HIV-1 genome nuclear import is mediated by a central DNA flap," Cell, 101(2):173-185.
Zhan et al., 2001, "Insulator: from chromatin domain boundary to gene regulation," Hum Genet, 109(5):471-478.
Zufferey et al., 1999, "Woodchuck hepatitis virus post-transcriptional regulatory element enhances expression of transgenes delivered by retroviral vectors," J Virol., 73(4):2886-2892.
Requirement for Species Election dated Jun. 24, 2016 for U.S. Appl. No. 14/653,650 (6 pages).
Response to Requirement for Species Election filed Aug. 22, 2016 for U.S. Appl. No. 14/653,650 (6 pages).
Non-Final Office Action with List of References dated Sep. 16, 2016 for U.S. Appl. No. 14/653,650 (21 pages).
Response to Non-Final Office Action filed Feb. 22, 2017 for U.S. Appl. No. 14/653,650 (12 pages).
Final Office Action with List of References dated May 4, 2017 for U.S. Appl. No. 14/653,650 (16 pages).
Response to Final Office Action filed Nov. 3, 2017 for U.S. Appl. No. 14/653,650 (9 pages).
Non-Final Office Action with List of References dated Dec. 18, 2017 for U.S. Appl. No. 14/653,650 (10 pages).
Response to Non-Final Office Action filed Jun. 15, 2018 for U.S. Appl. No. 14/653,650 (14 pages).
Notice of Allowance with Examiner's Comments dated Jul. 31, 2018 for U.S. Appl. No. 14/653,650 (9 pages).
Non-Final Office Action with List of References dated Sep. 21, 2020 for U.S. Appl. No. 16/175,747 (12 pages).
Requirement for Species Election dated Sep. 2, 2016 for U.S. Appl. No. 14/765,896 (11 pages).
Response to Requirement for Species Election filed Jan. 27, 2017 for U.S. Appl. No. 14/765,896 (2 pages).
Non-Final Office Action with List of References dated Apr. 27, 2017 for U.S. Appl. No. 14/765,896 (21 pages).
Response to Non-Final Office Action filed Oct. 26, 2017 for U.S. Appl. No. 14/765,896 (12 pages).
Final Office Action with List of References dated Nov. 29, 2017 for U.S. Appl. No. 14/765,896 (24 pages).
Non-Final Office Action with List of References dated Jun. 20, 2019 for U.S. Appl. No. 15/990,561 (19 pages).
Response to Non-Final Office Action filed Dec. 19, 2019 for U.S. Appl. No. 15/990,561 (14 pages).
Final Office Action dated Jan. 3, 2020 for U.S. Appl. No. 15/990,561 (19 pages).
Response to Non-Final Office Action filed Jul. 2, 2020 for U.S. Appl. No. 15/990,561 (18 pages).
Non-Final Office Action dated Oct. 16, 2020 for U.S. Appl. No. 15/990,561 (20 pages).
Requirement for Restriction and Species Election dated Dec. 21, 2016 for U.S. Appl. No. 14/775,891 (9 pages).
Response to Requirement for Restriction and Species Election filed Feb. 13, 2017 for U.S. Appl. No. 14/775,891 (8 pages).
Non-Final Office Action with List of References dated Apr. 25, 2017 for U.S. Appl. No. 14/775,891 (18 pages).
Response to Non-Final Office Action filed Oct. 24, 2017 for U.S. Appl. No. 14/775,891 (10 pages).
Notice of Allowance with Examiner's Amendment and Examiner Initiated Interview Summary dated Jan. 25, 2018 for U.S. Appl. No. 14/775,891 (9 pages).
Notice of Allowance with Examiner's Comment dated May 21, 2018 for U.S. Appl. No. 14/775,891 (9 pages).
Notice of Allowance with Examiner's Comment dated Nov. 20, 2018 for U.S. Appl. No. 14/775,891 (9 pages).
Requirement for Restriction and Species Election with List of References dated Nov. 19, 2019 for U.S. Appl. No. 15/502,752 (8 pages).
Non-Final Office Action dated Apr. 1, 2020 for U.S. Appl. No. 15/502,752 (10 pages).
Requirement for Restriction and Species Election dated Dec. 27, 2018 for U.S. Appl. No. 15/541,006 (8 pages).
Response to Requirement for Restriction and Species Election filed Apr. 29, 2019 for U.S. Appl. No. 15/541,006 (9 pages).
Non-Final Office Action with List of References dated Aug. 19, 2019 for U.S. Appl. No. 15/541,006 (13 pages).

* cited by examiner

MODIFIED T LYMPHOCYTES COMPRISING A CD52 ANTIBODY-INDUCIBLE CASPASE AND METHODS OF APOPTOSIS

This application is a divisional of U.S. patent application Ser. No. 16/276,581, filed Feb. 14, 2019, which is a divisional of U.S. patent application Ser. No. 14/775,891, filed Sep. 14, 2015, now U.S. Pat. No. 10,238,690, which is a U.S. National Stage of International Patent Application No. PCT/US2014/027039, filed Mar. 14, 2014, which claims the benefit of U.S. Provisional Patent Application No. 61/794,294, filed Mar. 15, 2013, the disclosure of each of which is incorporated by reference herein in its entirety.

SEQUENCE LISTING

This application incorporates by reference in its entirety the Computer Readable Form (CRF) of a Sequence Listing in ASCII text format submitted via EFS-Web. The Sequence Listing text file submitted via EFS-Web is entitled 14247-637-999_SEQ_LISTING.txt, was created on Mar. 3, 2021, and is 3,200 bytes in size.

1. FIELD

The disclosure herein relates to the field of immunology, and more specifically, to the modification of T lymphocytes or other immune cells.

2. BACKGROUND

T lymphocytes recognize and interact with specific antigens, including tumor-associated or tumor-specific antigens. Because T lymphocytes are able to kill tumor cells, the last 25 years has seen a great deal of interest in targeting tumor cells with T lymphocytes, either antigen-specific T lymphocytes, or T lymphocytes genetically modified to express one or more chimeric antigen receptors (CARs; see, e.g., Eshhar, U.S. Pat. No. 7,741,465; Eshhar, U.S. Patent Application Publication No. 2012/0093842). However, given the ability of T lymphocytes to kill not only tumor cells displaying a certain antigen but normal cells displaying the same antigen, it is desirable to incorporate into the T lymphocytes a safety mechanism that enables rapid killing of the cells after administration to a patient should off-target effects prove deleterious to the patient.

While a system to kill T cells has been described (Straathof et al. (2005) *Blood* 105(11):4247-4254), this system was dependent upon specific and difficult-to-make protein modifications, rendering the system undesirable for practical use. As such, there exists a need in the art for a safety system to rapidly kill therapeutic T lymphocytes that are relatively simple and straightforward to construct. T lymphocytes comprising such a safety system are provided herein.

3. SUMMARY

Provided herein are genetically modified cells, for example immune cells, such as T lymphocytes, e.g., human T lymphocytes, that comprise an artificial multimerizable, e.g., dimerizable, polypeptide (referred to herein as a "cell death polypeptide") that, when multimerized, e.g., dimerized, by a multimerizing agent, e.g., dimerizing agent, generates an apoptosis-inducing signal in a cell, e.g., a T lymphocyte, that expresses the polypeptide, resulting in cell death, e.g., via apoptosis. Without wishing to be bound by any particular mechanism or theory, it is thought that when a sufficient number of a plurality of cell death polypeptides of the cell are multimerized, e.g., dimerized, that the aggregate apoptosis-inducing signal thereby generated is sufficient to kill the cell, e.g., cause the cell to undergo apoptosis.

The cell death polypeptides provided herein may be used in conjunction with any cells, in particular, any mammalian cells, for example, any human cells. For example, such cell death polypeptides provide, for example, a useful safety feature for cell therapeutics. As such, the cell death polypeptides can, for example, be important for a drug product comprising a cell therapeutic, e.g., a chimeric antigen receptor-expressing CAR T lymphocytes, because the cell death polypeptides enable rapid killing of the cell therapeutic, e.g., the T lymphocytes, should such rapid killing become desirable, e.g., in the event administration of the cells causes any unwanted or deleterious effects in a patient receiving them, or if the presence of the cell therapeutic, e.g., the T lymphocytes, in a subject is no longer necessary. Thus, in certain embodiments, the cell death polypeptides provided herein can be used in conjunction with any administrable cells, for example cell therapeutics, such as mammalian cell therapeutics, e.g., human cell therapeutics. Non-limiting examples of cells in which the cell death polypeptides and multimerizing or dimerizing agents may be used include, but are not limited to, natural killer (NK) cells, dendritic cells (DC), placental stem cells (e.g., the placental stem cells disclosed in U.S. Pat. Nos. 7,468,276; 8,057,788 and 8,202,703, the disclosures of which are hereby incorporated by reference in their entireties), mesenchymal-like stem cells from umbilical cord blood, placental blood, peripheral blood, bone marrow, dental pulp, adipose tissue, osteochondral tissue, and the like; embryonic stem cells, embryonic germ cells, neural crest stem cells, neural stem cells, and differentiated cells (e.g., fibroblasts, etc.). The cell death polypeptides, and multimerizing or dimerizing agents, may also be used in tumor cell lines, e.g., for animal model experimental purposes.

Typically, the cell death polypeptide is multimerizable or dimerizable using an administrable multimerizing or dimerizing agent, e.g., a small molecule, polypeptide (other than the cell death polypeptide) such as an antibody, an oligonucleotide, or a polysaccharide. The cell death polypeptides do not comprise a FK506 binding protein (FKBP), functional portion thereof, of modified form thereof, and the multimerizing agent or dimerizing agent is not an FKBP ligand.

In a first aspect, provided herein is a cell, e.g., a T lymphocyte, comprising a cell death polypeptide comprising an apoptosis-inducing domain, wherein said cell death polypeptide is multimerizable using a multimerizing agent, wherein when said multimerizing agent multimerizes said polypeptide, an apoptosis-inducing signal is generated in said cell. In a specific embodiment, said multimerizing agent is a dimerizing agent; that is, the multimerizing agent causes the cell death polypeptide to dimerize. In another specific embodiment, when said dimerizing agent dimerizes said polypeptide, an apoptosis-inducing signal is generated in said cell.

In certain embodiments, said cell death polypeptide is a transmembrane polypeptide comprising an extracellular domain, a transmembrane domain, and an intracellular domain comprising said apoptosis-inducing domain. In particular embodiments, the apoptosis-inducing domain of the cell death polypeptide is or comprises a caspase, e.g., caspase 9, caspase 8, or caspase 3, for example a human caspase 9, caspase 8, or caspase 3.

In certain embodiments, the dimerizing agent is a polypeptide comprising at least two sites that specifically bind to a cell death polypeptide, e.g., an extracellular domain of a cell death polypeptide. In particular embodiments, the polypeptide is an antibody, e.g., an antibody comprising at least two epitope or mimotope binding sites. In certain embodiments, only the antigen binding domain of an antibody is used as a multimerizing or dimerizing agent. In certain embodiments, an extracellular domain of a cell death polypeptide comprises at least one epitope or mimotope to which the antibody specifically binds. In particular embodiments, the antibody is a bispecific antibody comprising two different epitope or mimotope binding sites that bind two different epitopes or mimotopes present on an extracellular domain of a cell death polypeptide. In certain embodiments, the antibody is an IgG or an IgM antibody. In a particular embodiment, an antibody useful as a multimerizing or dimerizing agent is one that has been approved by the United States Food and Drug Administration for any use.

In one embodiment, an antibody useful as a multimerizing or dimerizing agent is one that specifically binds to a CD20 epitope or mimotope, e.g., a human CD20 epitope or mimotope, and an extracellular domain of a cell death polypeptide comprises a CD20 epitope or mimotope to which the antibody specifically binds. In certain specific embodiments, the antibody is rituximab and an extracellular domain of a cell death polypeptide comprises a CD20 epitope or a CD20 mimotope that specifically binds to said rituximab. In another specific embodiment, the antibody is tositumumab and an extracellular domain of a cell death polypeptide comprises a CD20 epitope or a CD20 mimotope that specifically binds to said tositumumab. In yet another embodiment, the antibody is ibritumomab and an extracellular domain of a cell death polypeptide comprises a CD20 epitope or a CD20 mimotope that specifically binds to said ibritumomab. In still another embodiment, the antibody is ofatumumab and an extracellular domain of a cell death polypeptide comprises a CD20 epitope or a CD20 mimotope that specifically binds to said ofatumumab.

In another specific embodiment, the antibody is alemtuzumab and an extracellular domain of a cell death polypeptide comprises a CD52 epitope or a CD52 mimotope that specifically binds to said alemtuzumab. In yet another embodiment, the antibody is basiliximab and an extracellular domain of the cell death polypeptide comprises a CD25 epitope or a CD25 mimotope that specifically binds to said basiliximab. In another embodiment, the antibody is daclizumab and an extracellular domain of a cell death polypeptide comprises a CD25 epitope or a CD25 mimotope that specifically binds to said daclizumab. In still another embodiment, the antibody is brentuximab and an extracellular domain of a cell death polypeptide comprises a CD30 epitope or a CD30 mimotope that specifically binds to said brentuximab. In another embodiment, the antibody is belimumab and an extracellular domain of a cell death polypeptide comprises a B-cell activating factor (BAFF) epitope or a BAFF mimotope that specifically binds to said belimumab. In another embodiment, the antibody is cetuximab and an extracellular domain of a cell death polypeptide comprises an epidermal growth factor receptor (EGFR) epitope or an EGFR mimotope that specifically binds to said cetuximab. In yet another embodiment, the antibody is panitumumab and an extracellular domain of a cell death polypeptide comprises an epidermal growth factor receptor (EGFR) epitope or an EGFR mimotope that specifically binds to said panitumumab. In another embodiment, the antibody is efalizumab and an extracellular domain of a cell death polypeptide comprises an epitope of CD11a or a mimotope of CD11a that specifically binds to said efalizumab. In still another embodiment, the antibody is ipilimumab and an extracellular domain of a cell death polypeptide comprises a CD152 epitope or CD152 mimotope that specifically binds to said ipilimumab. In still another embodiment, the antibody is natalizumab and an extracellular domain of a cell death polypeptide comprises an epitope of alpha-4 integrin or a mimotope of alpha 4 integrin that specifically binds to said natalizumab. In another embodiment, the antibody is basiliximab and an extracellular domain of a cell death polypeptide comprises a CD25 epitope or CD25 mimotope that specifically binds to said basiliximab.

In certain embodiments, when a multimerizing agent or a dimerizing agent binds to at least two cell death polypeptides, dimerization or multimerization of the cell death polypeptides occurs, e.g., dimerization or multimerization of the cell death polypeptides occurs. In certain embodiments, an extracellular domain of a cell death polypeptide is or comprises a receptor or a ligand-binding portion thereof. In a specific embodiment, a multimerizing agent or dimerizing agent is or comprises at least two ligands for said receptor or ligand binding portion thereof. In another specific embodiment, said multimerizing agent or dimerizing agent binds to said receptor or said ligand binding portion thereof on two of the cell death polypeptides, and said polypeptides are multimerized or dimerized, e.g., the intracellular domains of said polypeptides are multimerized or dimerized. In particular embodiments the cell death polypeptides comprise intracellular domains comprising a caspase domain, and multimerization or dimerization of the caspase domains occurs. In specific embodiments, said multimerization or dimerization, for example, multimerization or dimerization of intracellular domains, e.g., multimerization or dimerization of caspase domains, initiates an apoptosis-inducing signal in said cell, e.g., T lymphocyte.

In specific embodiments, when an antibody specifically binds to an epitope or mimotope of at least two cell death polypeptides, dimerization of the cell death polypeptides occurs, e.g., dimerization of the intracellular domains of the cell death polypeptides occurs. In particular embodiments the cell death polypeptides comprise intracellular domains comprising a caspase domain, and dimerization of the caspase domains occurs. In specific embodiments, said dimerization, for example, dimerization of intracellular domains, e.g., dimerization of caspase domains, initiates an apoptosis-inducing signal in said cell, e.g., T lymphocyte.

In certain other embodiments of the cell, e.g., T lymphocyte, said extracellular domain of the cell death polypeptide comprises a ligand for a receptor. In a specific embodiment, said multimerizing agent or dimerizing agent comprises at least two receptors or ligand-binding portions thereof that bind to said ligand. In a specific embodiment, when said multimerizing agent or dimerizing agent binds to said receptor or said ligand binding portion thereof on at least two of the cell death polypeptides, said polypeptides are multimerized or dimerized. In a specific embodiment, when the cell death polypeptides are multimerized or dimerized, an apoptosis-inducing signal is generated in said cell.

In certain other embodiments, an extracellular domain of a cell death polypeptide comprises an artificial oligonucleotide sequence. For example, in particular embodiments, a modified cell, e.g., T lymphocyte, comprises a cell death polypeptide comprising an extracellular domain that comprises an artificial oligonucleotide sequence. In a specific embodiment, a multimerizing or dimerizing agent is or comprises at least one multimerizing or dimerizing oligonucleotide comprising a first oligonucleotide and a second oligonucleotide, optionally joined by a linker, wherein said first oligonucleotide and said second oligonucleotide are complementary to said artificial oligonucleotide sequence. In certain specific embodiments, said first oligonucleotide and said second oligonucleotide have the same sequence. In specific embodiments, said first oligonucleotide and said second oligonucleotide are joined in a head-to-head or tail-to-tail conformation. In specific embodiments, when said multimerizing or dimerizing oligonucleotide of said multimerizing agent or dimerizing agent hybridizes to the artificial oligonucleotide sequence of two of said cell death polypeptides, the cell death polypeptides are multimerized or dimerized. In another specific embodiment, when the cell death polypeptides are multimerized or dimerized, an apoptosis-inducing signal is generated in said cell. In particular embodiments, the cell death polypeptides comprise intracellular caspase domains, and when the intracellular caspase domains are multimerized or dimerized, an apoptosis-inducing signal is generated in said cell.

In certain other embodiments of the cell, e.g., T lymphocyte, said multimerizing or dimerizing agent is an artificial polypeptide comprising two or more binding domains joined by one or more linkers.

In a specific embodiment, provided herein is a cell, e.g., a T lymphocyte, comprising a cell death polypeptide comprising an extracellular domain comprising an epitope, a transmembrane domain, and an intracellular domain comprising a caspase 9, e.g., a human caspase 9, or a functional portion thereof. In another specific embodiment, provided herein is a cell, e.g., a T lymphocyte, comprising an artificial polypeptide comprising an extracellular domain comprising a receptor or ligand-binding portion thereof, and an intracellular domain comprising a caspase 9, e.g., a human caspase 9, or a functional portion thereof. In another specific embodiment, provided herein is a cell, e.g., a T lymphocyte, comprising an artificial polypeptide comprising an extracellular domain comprising a ligand or a receptor-binding portion thereof, wherein said ligand binds a receptor or ligand-binding portion thereof, and an intracellular domain comprising a caspase 9, e.g., a human caspase 9, or functional portion thereof. In a specific embodiment, said cell is a T lymphocyte.

In another aspect, provided herein is cell, e.g., a T lymphocyte, safety system comprising a cell comprising (a) a cell death polypeptide comprising an extracellular domain comprising an epitope, a transmembrane domain, and an intracellular domain comprising a caspase or a functional portion thereof; and (b) a dimerizing agent comprising two epitope-binding or mimotope-binding domains that when contacted with two of said cell death polypeptides dimerizes said polypeptides, wherein said caspase is caspase 3, caspase 8 or caspase 9, e.g., human caspase 3, caspase 8, or caspase 9, and wherein said dimerization generates an apoptosis-inducing signal in said cell. In a specific embodiment, said cell is a T lymphocyte.

In another embodiment, provided herein is a cell, e.g., a T lymphocyte, safety system comprising (a) a cell comprising an artificial polypeptide comprising an extracellular domain comprising a receptor or ligand-binding portion thereof, and an intracellular domain comprising a caspase or a functional portion thereof; and (b) a dimerizing agent comprising two ligands that bind to said receptor or ligand-binding portion thereof, wherein when said dimerizing agent is contacted with two of said polypeptides said dimerizing agent dimerizes said polypeptides, wherein said caspase is caspase 3, caspase 8 or caspase 9, e.g., human caspase 3, caspase 8, or caspase 9, and wherein said dimerization generates an apoptosis-inducing signal in said cell. In a specific embodiment, said cell is a T lymphocyte.

In another embodiment, provided herein is a cell, e.g., a T lymphocyte, safety system comprising (a) a cell comprising an artificial cell death polypeptide comprising an extracellular domain comprising a ligand or a receptor-binding portion thereof, and an intracellular domain comprising a caspase or functional portion thereof; and (b) a dimerizing agent comprising two receptors or ligand-binding portions thereof that bind to said ligand or receptor-binding portion thereof, wherein when said dimerizing agent is contacted with two of said polypeptides said dimerizing agent dimerizes said polypeptides, wherein said caspase is caspase 3, caspase 8 or caspase 9, e.g., human caspase 3, caspase 8, or caspase 9, and wherein said dimerization generates an apoptosis-inducing signal in said cell. In a specific embodiment, said cell is a T lymphocyte.

In a specific embodiment of any of the embodiments herein, when a plurality of said apoptosis-inducing signals are generated in said cell, e.g., T lymphocyte, said signal is sufficient to kill said cell. In a specific embodiment, said cell is a T lymphocyte.

In another aspect, further provided herein is a method of killing a cell, e.g., a T lymphocyte, wherein said cell comprises a plurality of artificial cell death polypeptides each comprising an apoptosis-inducing domain, wherein the cell death polypeptides are multimerizable or dimerizable using a multimerizing agent or dimerizing agent that is not an FK506 binding protein (FKBP) ligand, and wherein when said multimerizing agent or dimerizing agent multimerizes or dimerizes said polypeptide, an apoptosis-inducing signal is generated in said T lymphocyte, comprising contacting said cell with an amount of said multimerizing agent or dimerizing agent sufficient for said plurality of the cell death polypeptides to multimerize or dimerize and generate an aggregate apoptosis-inducing signal sufficient to kill said cell. In certain embodiments, the cell death polypeptide is a transmembrane polypeptide comprising an extracellular domain, a transmembrane domain, and an intracellular domain comprising said apoptosis-inducing domain. In specific embodiments, said apoptosis-inducing domain of said polypeptide is or comprises a caspase, e.g., caspase 3, caspase 8 or caspase 9, for example a human caspase 9, caspase 8, or caspase 3. In specific embodiments, the multimerizing agent or dimerizing agent is a protein, an oligonucleotide or a polysaccharide. In a specific embodiment, said cell is a T lymphocyte.

In certain embodiments, the multimerizing agent or dimerizing agent is a protein, an oligonucleotide, or a polysaccharide. In specific embodiments, the multimerizing agent or dimerizing agent is a polypeptide comprising at least two sites that specifically bind to a cell death polypeptide, e.g., an extracellular domain of a cell death polypeptide. In particular embodiments, the polypeptide is an antibody, e.g., an antibody that comprises at least two epitope-binding sites or at least two mimotope-binding sites. In certain embodiments, an extracellular domain of a cell death polypeptide comprises at least one epitope or mimotope to which the antibody specifically binds. In particular embodiments, the antibody is a bispecific antibody comprising two different epitope or mimotope binding sites that bind two different epitopes or mimotopes present on an extracellular domain of a cell death polypeptide. In certain embodiments, the antibody is an IgG or an IgM antibody. In a specific embodiment, an antibody useful as a multimerizing or dimerizing agent is one that has been approved by the United States Food and Drug Administration for any use.

In a specific embodiment, when the multimerizing agent or dimerizing agent is an antibody, said antibody is one that specifically binds to a CD20 epitope or mimotope, e.g., a human CD20 epitope or mimotope, and said extracellular domain of a cell death polypeptide comprises a CD20 epitope or mimotope to which said antibody specifically binds. In certain specific embodiments, when the multimerizing agent or dimerizing agent is an antibody, said antibody is rituximab and said extracellular domain of the cell death polypeptide comprises a CD20 epitope or a CD20 mimotope that binds to said rituximab; said antibody is tositumumab and said extracellular domain of the cell death polypeptide comprises a CD20 epitope or a CD20 mimotope that binds to said tositumumab; said antibody is ibritumomab and said extracellular domain of the cell death polypeptide comprises a CD20 epitope or a CD20 mimotope that binds said ibritumomab; said antibody is ofatumumab and said extracellular domain of the cell death polypeptide comprises a CD20 epitope or a CD20 mimotope that binds said ofatumumab; said antibody is alemtuzumab and said extracellular domain of the cell death polypeptide comprises a CD52 epitope or a CD52 mimotope that binds to said alemtuzumab; said antibody is basiliximab and said extracellular domain of the cell death polypeptide comprises a CD25 epitope or a CD25 mimotope that binds said basiliximab; said antibody is daclizumab and said extracellular domain of the cell death polypeptide comprises a CD25 epitope or a CD25 mimotope that binds said daclizumab; said antibody is brentuximab and said extracellular domain of the cell death polypeptide comprises a CD30 epitope or a CD30 mimotope that binds said brentuximab; said antibody is belimumab and said extracellular domain of the cell death polypeptide comprises a B-cell activating factor (BAFF) epitope or a BAFF mimotope that binds said belimumab; said antibody is cetuximab and said extracellular domain of the cell death polypeptide comprises an epidermal growth factor receptor (EGFR) epitope or an EGFR mimotope that binds said cetuximab; said antibody is panitumumab and said extracellular domain of the cell death polypeptide comprises an epidermal growth factor receptor (EGFR) epitope or an EGFR mimotope that binds said panitumumab; said antibody is efalizumab and said extracellular domain of the cell death polypeptide comprises an epitope of CD11a or a mimotope of CD11a that binds to said efalizumab; said antibody is ipilimumab and said extracellular domain of the cell death polypeptide comprises a CD152 epitope or CD152 mimotope that binds said ipilimumab; said antibody is natalizumab and said extracellular domain of the cell death polypeptide comprises an epitope of alpha-4 integrin or a mimotope of alpha 4 integrin that binds said natalizumab; or said antibody is basiliximab and said extracellular domain of the cell death polypeptide comprises a CD25 epitope or CD25 mimotope that binds said basiliximab. In a specific embodiment of any of the above embodiments, when said antibody binds to said epitope or mimotope on at least two of said cell death polypeptides, the intracellular domains of said polypeptides, and/or the respective caspases in said intracellular domains multimerize or dimerize. In specific embodiments, when said antibody specifically binds to an epitope or mimotope of at least two cell death polypeptides, dimerization of the cell death polypeptides occurs, e.g., dimerization of the intracellular domains of the cell death polypeptides occurs. In particular embodiments the cell death polypeptides comprise intracellular domains comprising a caspase domain, and dimerization of the caspase domains occurs. In specific embodiments, said dimerization, for example, dimerization of intracellular domains, e.g., dimerization of caspase domains, initiates an apoptosis-inducing signal in said cell, e.g., T lymphocyte.

In certain specific embodiments, said extracellular domain of the cell death polypeptide is or comprises a receptor or a ligand-binding portion thereof. In such embodiments, said multimerizing agent or dimerizing agent comprises at least two ligands for said receptor or ligand binding portion thereof. In specific embodiments, when said multimerizing agent or dimerizing agent binds to said receptor or said ligand binding portion thereof on at least two of said cell death polypeptides, said polypeptides are multimerized or dimerized. In specific embodiments, said multimerization or dimerization of said polypeptides initiates an apoptosis-inducing signal in said cell, e.g., T lymphocyte.

In certain specific embodiments, said extracellular domain of the cell death polypeptide comprises a ligand for a receptor. In such embodiments, said multimerizing agent or dimerizing agent comprises at least two receptors or ligand-binding portions thereof that bind to said ligand. In specific embodiments, when said multimerizing agent or dimerizing agent binds to said receptor or said ligand binding portion thereof on two or more of said polypeptides, the intracellular domains in said polypeptides and/or the caspase domains of said polypeptides are multimerized or dimerized. In specific embodiments, said multimerization or dimerization of said intracellular domains and/or caspase domains initiates an apoptosis-inducing signal is generated in said cell, e.g., T lymphocyte.

In certain embodiments, said extracellular domain of said cell death polypeptide comprises an artificial oligonucleotide sequence. For example, in particular embodiments, said cell death polypeptide comprises an extracellular domain that comprises an artificial oligonucleotide sequence. In a specific embodiment, a multimerizing or dimerizing agent is or comprises at least one multimerizing or dimerizing oligonucleotide comprising a first oligonucleotide and a second oligonucleotide, optionally joined by a linker, wherein said first oligonucleotide and said second oligonucleotide are complementary to said artificial oligonucleotide sequence. In certain specific embodiments, said first oligonucleotide and said second oligonucleotide have the same sequence. In specific embodiments, said first oligonucleotide and said second oligonucleotide are joined in a head-to-head or tail-to-tail conformation. In specific embodiments, when said multimerizing or dimerizing oligonucleotide of said multimerizing agent or dimerizing agent hybridizes to the artificial oligonucleotide sequence of two of said cell death polypeptides, the cell death polypeptides are multimerized or dimerized. In another specific embodiment, when the cell death polypeptides are multimerized or dimerized, an apoptosis-inducing signal is generated in said cell. In particular embodiments, the cell death polypeptides comprise intracellular caspase domains, and when the intracellular caspase domains are multimerized or dimerized, an apoptosis-inducing signal is generated in said cell. In a specific embodiment, said cell is a T lymphocyte.

In a specific embodiment of any of the embodiments herein, when a plurality of said apoptosis-inducing signals are generated in said T lymphocyte, said signal is sufficient to kill said cell, e.g., T lymphocyte.

In other embodiments, said multimerizing agent or dimerizing agent is an artificial polypeptide comprising two or more binding domains joined by one or more linkers.

In a specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said cell death polypeptide is dimerizable using an antibody, and wherein when said antibody dimerizes said polypeptide, an apoptosis-inducing signal is generated in said cell, comprising contacting said cell with an amount of said antibody sufficient to dimerize a sufficient number of said plurality of artificial polypeptides to dimerize and generate an aggregate apoptosis-inducing signal sufficient to kill said cell. In a specific embodiment, said cell is a T lymphocyte.

In another specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprises an extracellular domain comprising a receptor or ligand-binding portion thereof that bind a ligand, wherein said polypeptide is dimerizable using a dimerizing agent comprising two said ligands, and wherein when said dimerizing agent dimerizes two of said polypeptides, an apoptosis-inducing signal is generated in cell, comprising contacting said cell with an amount of said dimerizing agent sufficient to dimerize a sufficient number of said plurality of artificial cell death polypeptides to dimerize and generate an aggregate apoptosis-inducing signal sufficient to kill said cell. In a specific embodiment, said cell is a T lymphocyte.

In another specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprises an extracellular domain comprising a ligand or receptor-binding portion thereof that bind a receptor or ligand-binding portion thereof, wherein said polypeptides are dimerizable using a dimerizing agent comprising two said receptors or ligand-binding portion thereof, and wherein when said dimerizing agent dimerizes two of said polypeptides, an apoptosis-inducing signal is generated in said cell, comprising contacting said cell with an amount of said dimerizing agent sufficient to dimerize a sufficient number of said plurality of artificial polypeptides to dimerize and generate an aggregate apoptosis-inducing signal sufficient to kill said cell. In a specific embodiment, said cell is a T lymphocyte.

In another specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprising an extracellular domain comprising an artificial oligonucleotide, wherein said plurality of polypeptides are dimerizable using a dimerizing agent comprising an oligonucleotide comprising a first oligonucleotide and a second oligonucleotide, wherein said first oligonucleotide and said second oligonucleotide have the same nucleotide sequence, and wherein said first oligonucleotide and second oligonucleotide optionally are joined by a linker, and wherein said first oligonucleotide and said second oligonucleotide are complementary to said artificial oligonucleotide in said extracellular domain of said polypeptide, and wherein when said dimerizing agent dimerizes two of said cell death polypeptides, an apoptosis-inducing signal is generated in said cell, comprising contacting said cell with an amount of said dimerizing agent sufficient to dimerize a sufficient number of said plurality of artificial polypeptides to dimerize and generate an aggregate apoptosis-inducing signal sufficient to kill said cell. In a specific embodiment, said cell is a T lymphocyte.

In certain embodiments, the cells (e.g., T lymphocytes) killed in accordance with the methods described herein comprise a polypeptide that acts to target the cell to a particular antigen, e.g., a tumor-associated antigen or tumor-specific antigen, wherein said polypeptide, when bound to said antigen, causes the cell to kill a cell displaying said antigen, for example, a chimeric antigen receptor (CAR). T lymphocytes comprising CARs are referred to herein as CAR-T lymphocytes. The chimeric antigen receptors typically comprise (i) an intracellular domain (e.g., cytoplasmic domain) of an endogenous protein expressed on the surface of lymphocytes and that triggers the activation and/or proliferation of said lymphocytes, (ii) a transmembrane domain, and (iii) an extracellular domain that binds to an antigen of interest, e.g., a tumor-associated antigen or tumor-specific antigen. The CAR-T lymphocytes also typically comprise one or more co-stimulatory domains. In certain embodiments, a CAR-T lymphocyte comprises at least two CAR polypeptides, at least one of which provides a primary stimulatory signal to the CAR-T lymphocyte, and at least one that provides a costimulatory signal to the CAR-T lymphocyte. CAR-T lymphocytes comprising a cell death polypeptide and comprising specific embodiments of CARs are provided below.

In another aspect, provided herein are methods of treating an individual having a disease or disorder, wherein the disease or disorder is characterized, or is characterizable, by cells expressing an antigen, comprising administering to the individual cells, e.g., T lymphocytes, expressing a polypeptide, as described herein. In certain embodiments, when the modified cells, e.g., modified T lymphocytes described herein are administered to a subject in need thereof, the combination of multimerizing agent and cell death polypeptide selected are chosen such that they are compatible with the patient population (or subpopulation) in which the cells, e.g., T lymphocytes, have been administered. By way of example only, if the multimerizing agent selected is the antibody rituximab, then in certain embodiments the patient population is individuals having a cancer of the B cells, e.g., B cell lymphoma.

4. DETAILED DESCRIPTION

4.1. Cells Comprising Cell Death Polypeptides

Provided herein are genetically modified cells, for example immune cells, such as T lymphocytes, e.g., human T lymphocytes, that comprise an artificial multimerizable, e.g., dimerizable, polypeptide (referred to herein as a "cell death polypeptide") that, when multimerized, e.g., dimerized, by a multimerizing agent, e.g., dimerizing agent, generates an apoptosis-inducing signal in a cell, e.g., a T lymphocyte, that expresses the polypeptide, resulting in cell death, e.g., via apoptosis. Without wishing to be bound by any particular mechanism or theory, it is thought that when a sufficient number of a plurality of cell death polypeptides of the cell are multimerized, e.g., dimerized, that the aggregate apoptosis-inducing signal thereby generated is sufficient to kill the cell, e.g., cause the cell to undergo apoptosis. In a specific embodiment, the genetically modified cells provided herein are T lymphocytes.

In certain embodiments, the cell death polypeptide can be multimerized or dimerized by an administrable multimerizing agent or dimerizing agent, e.g., a protein (e.g., antibody, receptor or ligand-binding portion thereof, a ligand or receptor-binding portion thereof), oligonucleotide, or the like. In certain embodiments, the multimerizing agent is not a small molecule. The multimerizing or dimerizing agent can be used to kill T lymphocytes comprising the cell death polypeptide either in vitro or in vivo.

Thus, in a first aspect, provided herein is a T lymphocyte comprising an artificial polypeptide (cell death polypeptide) comprising an apoptosis-inducing domain, wherein said cell death polypeptide is multimerizable using a multimerizing agent, wherein said multimerizing agent is not an FK506 binding protein (FKBP) ligand, and wherein when said multimerizing agent multimerizes said polypeptide, an apoptosis-inducing signal is generated in said T lymphocyte. In a specific embodiment, said multimerizing agent is a dimerizing agent; that is, the multimerizing agent causes the cell death polypeptide to dimerize. In another specific embodiment, when said dimerizing agent dimerizes said cell death polypeptide, an apoptosis-inducing signal is generated in said T lymphocyte. The cell death polypeptide does not comprise an FK506 binding protein, functional portion thereof, or modified form thereof.

In certain embodiments, said cell death polypeptide is a transmembrane polypeptide comprising an extracellular domain, a transmembrane domain, and an intracellular domain comprising said apoptosis-inducing domain. In certain embodiments, the apoptosis-inducing domain of the cell death polypeptide can be, for example, any protein or portion thereof that when dimerized initiates an apoptosis-inducing signal in the cell. In certain embodiments, the apoptosis-inducing domain is any caspase that homodimerizes, and preferably is or comprises a caspase, e.g., caspase 9, caspase 8, or caspase 3 (e.g., human caspase 9, caspase 8, or caspase 3). The amino acid sequences of human caspases, including human caspase 9, human caspase 8, and human caspase 3 are well known in the art. For example, human caspase 3 has been assigned NCBI Gene ID: 836; human caspase 8 has been assigned NCBI Gene ID: 841; and human caspase 9 has been assigned NCBI Gene ID: 842. In certain embodiments, the intracellular domain that is, or comprises, a caspase domain, and the extracellular domain, which comprises the epitope or mimotope, are joined by a CD8α stalk or CD8β stalk, at least part of which can function as a transmembrane domain.

In certain embodiments, the dimerizing agent is a polypeptide comprising at least two sites that specifically bind to a cell death polypeptide, e.g., an extracellular domain of a cell death polypeptide. In particular embodiments, the polypeptide is an antibody, e.g., an antibody comprising at least two epitope or mimotope binding sites. In certain embodiments, only the antigen binding domain of an antibody is used as a multimerizing or dimerizing agent. In certain embodiments, an extracellular domain of a cell death polypeptide comprises at least one epitope or mimotope to which the antibody specifically binds. In particular embodiments, the antibody is a bispecific antibody comprising two different epitope or mimotope binding sites that bind two different epitopes or mimotopes present on an extracellular domain of a cell death polypeptide. In certain embodiments, the antibody is an IgG or an IgM antibody. Artificial antibody constructs comprising epitope-binding or mimotope-binding domains from antibodies, optionally joined by one or more linkers, may also be used.

In a specific embodiment, said antibody, useful as a multimerizing or dimerizing agent, has been approved by a governmental regulatory authority, e.g., the United States Food and Drug Administration for any use. This ensures, e.g., that the antibody, when used as a dimerizing or multimerizing agent, has a known toxicity and patient safety profile. Any combination of antibody and associated target may be used in the T lymphocytes provided herein. In one embodiment, an antibody useful as a multimerizing or dimerizing agent is one that specifically binds to a CD20 epitope or mimotope, e.g., a human CD20 epitope or mimotope, and an extracellular domain of a cell death polypeptide comprises a CD20 epitope or mimotope to which the antibody specifically binds. In certain specific embodiments, the antibody is rituximab and an extracellular domain of a cell death polypeptide comprises a CD20 epitope or a CD20 mimotope that specifically binds to said rituximab. In another specific embodiment, the antibody is tositumumab and an extracellular domain of a cell death polypeptide comprises a CD20 epitope or a CD20 mimotope that specifically binds to said tositumumab. In yet another embodiment, the antibody is ibritumomab and an extracellular domain of a cell death polypeptide comprises a CD20 epitope or a CD20 mimotope that specifically binds to said ibritumomab. In still another embodiment, the antibody is ofatumumab and an extracellular domain of a cell death polypeptide comprises a CD20 epitope or a CD20 mimotope that specifically binds to said atumumab.

In another specific embodiment, the antibody is alemtuzumab and an extracellular domain of a cell death polypeptide comprises a CD52 epitope or a CD52 mimotope that specifically binds to said alemtuzumab. In yet another embodiment, the antibody is basiliximab and an extracellular domain of the cell death polypeptide comprises a CD25 epitope or a CD25 mimotope that specifically binds to said basiliximab. In another embodiment, the antibody is daclizumab and an extracellular domain of a cell death polypeptide comprises a CD25 epitope or a CD25 mimotope that specifically binds to said daclizumab. In still another embodiment, the antibody is brentuximab and an extracellular domain of a cell death polypeptide comprises a CD30 epitope or a CD30 mimotope that specifically binds to said brentuximab. In another embodiment, the antibody is belimumab and an extracellular domain of a cell death polypeptide comprises a B-cell activating factor (BAFF) epitope or a BAFF mimotope that specifically binds to said belimumab. In another embodiment, the antibody is cetuximab and an extracellular domain of a cell death polypeptide comprises an epidermal growth factor receptor (EGFR) epitope or an EGFR mimotope that specifically binds to said cetuximab. In yet another embodiment, the antibody is panitumumab and an extracellular domain of a cell death polypeptide comprises an epidermal growth factor receptor (EGFR) epitope or an EGFR mimotope that specifically binds to said panitumumab. In another embodiment, the antibody is efalizumab and an extracellular domain of a cell death polypeptide comprises an epitope of CD11a or a mimotope of CD11a that specifically binds to said efalizumab. In still another embodiment, the antibody is ipilimumab and an extracellular domain of a cell death polypeptide comprises a CD152 epitope or CD152 mimotope that specifically binds to said ipilimumab. In still another embodiment, the antibody is natalizumab and an extracellular domain of a cell death polypeptide comprises an epitope of alpha-4 integrin or a mimotope of alpha 4 integrin that specifically binds to said natalizumab. In another embodiment, the antibody is basiliximab and an extracellular domain of a cell death polypeptide comprises a CD25 epitope or CD25 mimotope that specifically binds to said basiliximab.

Ligands and receptors can be utilized in the construction of the cell death polypeptides provided herein, and multimerizing agents or dimerizing agents comprising the receptors' respective ligands can be used to multimerize or dimerize the polypeptides. In certain embodiments, when a multimerizing agent or a dimerizing agent binds to at least two cell death polypeptides, dimerization or multimerization of the cell death polypeptides occurs, e.g., dimerization or multimerization of the cell death polypeptides occurs. In certain embodiments, an extracellular domain of a cell death polypeptide is or comprises a receptor or a ligand-binding portion thereof. In a specific embodiment, a multimerizing agent or dimerizing agent is or comprises at least two ligands for said receptor or ligand binding portion thereof. In another specific embodiment, said multimerizing agent or dimerizing agent binds to said receptor or said ligand binding portion thereof on two of the cell death polypeptides, and said polypeptides are multimerized or dimerized, e.g., the intracellular domains of said polypeptides are multimerized or dimerized. In particular embodiments the cell death polypeptides comprise intracellular domains comprising a caspase domain, and multimerization or dimerization of the caspase domains occurs. In specific embodiments, said multimerization or dimerization, for example, multimerization or dimerization of intracellular domains, e.g., multimerization or dimerization of caspase domains, initiates an apoptosis-inducing signal in said cell, e.g., T lymphocyte.

In specific embodiments, when an antibody specifically binds to an epitope or mimotope of at least two cell death polypeptides, dimerization of the cell death polypeptides occurs, e.g., dimerization of the intracellular domains of the cell death polypeptides occurs. In particular embodiments the cell death polypeptides comprise intracellular domains comprising a caspase domain, and dimerization of the caspase domains occurs. In specific embodiments, said dimerization, for example, dimerization of intracellular domains, e.g., dimerization of caspase domains, initiates an apoptosis-inducing signal in said cell, e.g., T lymphocyte.

In certain other embodiments of the cell, e.g., T lymphocyte, said extracellular domain of the cell death polypeptide comprises a ligand for a receptor. In a specific embodiment, said multimerizing agent or dimerizing agent comprises at least two receptors or ligand-binding portions thereof that bind to said ligand. In a specific embodiment, when said multimerizing agent or dimerizing agent binds to said receptor or said ligand binding portion thereof on at least two of the cell death polypeptides, said polypeptides are multimerized or dimerized. In a specific embodiment, when the cell death polypeptides are multimerized or dimerized, an apoptosis-inducing signal is generated in said cell. In a specific embodiment, said cell is a T lymphocyte.

In certain other embodiments, an extracellular domain of a cell death polypeptide comprises an artificial oligonucleotide sequence. For example, in particular embodiments, a modified cell, e.g., T lymphocyte, comprises a cell death polypeptide comprising an extracellular domain that comprises an artificial oligonucleotide sequence. In a specific embodiment, a multimerizing or dimerizing agent is or comprises at least one multimerizing or dimerizing oligonucleotide comprising a first oligonucleotide and a second oligonucleotide, optionally joined by a linker, wherein said first oligonucleotide and said second oligonucleotide are complementary to said artificial oligonucleotide sequence. In certain specific embodiments, said first oligonucleotide and said second oligonucleotide have the same sequence. In specific embodiments, said first oligonucleotide and said second oligonucleotide are joined in a head-to-head or tail-to-tail conformation. In specific embodiments, when said multimerizing or dimerizing oligonucleotide of said multimerizing agent or dimerizing agent hybridizes to the artificial oligonucleotide sequence of two of said cell death polypeptides, the cell death polypeptides are multimerized or dimerized. In another specific embodiment, when the cell death polypeptides are multimerized or dimerized, an apoptosis-inducing signal is generated in said cell. In particular embodiments, the cell death polypeptides comprise intracellular caspase domains, and when the intracellular caspase domains are multimerized or dimerized, an apoptosis-inducing signal is generated in said cell. In a specific embodiment, said cell is a T lymphocyte.

In certain other embodiments of the T lymphocyte, the multimerizing or dimerizing agent is an artificial polypeptide comprising two or more binding domains joined by one or more linkers.

In a specific embodiment, provided herein is a cell, e.g., a T lymphocyte, comprising a cell death polypeptide comprising an extracellular domain comprising an epitope, a transmembrane domain, and an intracellular domain comprising a caspase 9, e.g., a human caspase 9, or a functional portion thereof. In another specific embodiment, provided herein is a cell, e.g., a T lymphocyte, comprising an artificial polypeptide comprising an extracellular domain comprising a receptor or ligand-binding portion thereof, and an intracellular domain comprising a caspase 9, e.g., a human caspase 9, or a functional portion thereof. In another specific embodiment, provided herein is a cell, e.g., a T lymphocyte, comprising an artificial polypeptide comprising an extracellular domain comprising a ligand or a receptor-binding portion thereof, wherein said ligand binds a receptor or ligand-binding portion thereof, and an intracellular domain comprising a caspase 9, e.g., a human caspase 9, or functional portion thereof. In a specific embodiment, said cell is a T lymphocyte.

In any of the embodiments herein, wherein the modified cells are T lymphocytes, the T lymphocytes may be CD4+ T lymphocytes or CD8+ T lymphocytes. The T lymphocytes may be, without genetic modification, specific for a particular antigen (e.g., a tumor-associated antigen, tumor-specific antigen, viral antigen, or the like). The T lymphocytes may be genetically modified to express one or more polypeptides, e.g., chimeric antigen receptors, that target the T lymphocyte to a specific antigen.

4.2. Methods of Killing Cells that Comprise Cell Death Polypeptides

The cell death polypeptides provided herein can be used in methods of killing cells, e.g., T lymphocytes, that comprise the cell death polypeptides. The cell death polypeptides provided herein may be used in conjunction with any cells, in particular, any mammalian cells, for example, any human cells. Such cell death polypeptides provide, for example, a useful safety feature for cell therapeutics. As such, the cell death polypeptides can, for example, be important for a drug product comprising a cell therapeutic, e.g., a chimeric antigen receptor-expressing CAR T lymphocytes, because the cell death polypeptides enable rapid killing of the cell therapeutic, e.g., the T lymphocytes, should such rapid killing become desirable, e.g., in the event administration of the cells causes any unwanted or deleterious effects in a patient receiving them, or if the presence of the cell therapeutic, e.g., the T lymphocytes, in a subject is no longer necessary. Thus, in certain embodiments, the cell death polypeptides provided herein can be used in conjunction with any administrable cells, for example cell therapeutics, such as mammalian cell therapeutics, e.g., human cell therapeutics. Non-limiting examples of cells in which the cell death polypeptides and multimerizing or dimerizing agents may be used include, but are not limited to, natural killer (NK) cells, dendritic cells (DC), placental stem cells (e.g., the placental stem cells disclosed in U.S. Pat. Nos. 7,468, 276; 8,057,788 and 8,202,703, the disclosures of which are hereby incorporated by reference in their entireties), mesenchymal-like stem cells from umbilical cord blood, placental blood, peripheral blood, bone marrow, dental pulp, adipose tissue, osteochondral tissue, and the like; embryonic stem cells, embryonic germ cells, neural crest stem cells, neural stem cells, and differentiated cells (e.g., fibroblasts, etc.). The cell death polypeptides, and multimerizing or dimerizing agents, may also be used in tumor cell lines, e.g., for animal model experimental purposes.

Cell killing by the cell death polypeptides described herein can take place either in vivo, e.g., in an individual to whom the cells, e.g., T lymphocytes, have been administered, or in vitro, e.g., in a laboratory, e.g., as part of quality control experiments. In one embodiment, provided herein is a method of killing a cell, e.g., a T lymphocyte, wherein said cell comprises a plurality of artificial cell death polypeptides each comprising an apoptosis-inducing domain, wherein said polypeptides are multimerizable or dimerizable using a multimerizing agent or dimerizing agent that is not an FK506 binding protein (FKBP) ligand, and wherein when said multimerizing agent or dimerizing agent multimerizes or dimerizes said polypeptide, an apoptosis-inducing signal is generated in said cell, comprising contacting said cell with an amount of said multimerizing agent or dimerizing agent sufficient for said plurality of artificial polypeptides to dimerize and generate an aggregate apoptosis-inducing signal sufficient to kill said cell. In certain embodiments, the cell death polypeptide is a transmembrane polypeptide comprising an extracellular domain, a transmembrane domain, and an intracellular domain comprising said apoptosis-inducing domain. In certain embodiments, the intracellular domain that is, or comprises, a caspase domain, and the extracellular domain, which comprises the epitope or mimotope, are joined by a CD8α stalk or CD8β stalk, at least part of which can function as a transmembrane domain. In certain specific embodiments of the method, the apoptosis-inducing domain of said polypeptide is or comprises a caspase, e.g., caspase 3, caspase 8, or caspase 9 (e.g., human caspase 9, caspase 8, or caspase 3).

The multimerizing agent or dimerizing agent used in the method can be any compound, other than a small molecule, that can dimerize or multimerizes a cell death polypeptide, e.g., a protein, an oligonucleotide or a polysaccharide. In certain embodiments, the multimerizing agent or dimerizing agent is an antibody, e.g., an antibody that comprises at least two epitope-binding sites or at least two mimotope-binding sites. In certain embodiments, only the antigen binding domain of an antibody is used as a multimerizing or dimerizing agent. In such embodiments, the extracellular domain of the cell death polypeptide comprises an epitope or mimotope to which the antibody binds. The antibody can be an antibody of any valence, but is preferably an IgG or an IgM antibody.

In a specific embodiment, said antibody, useful as a multimerizing or dimerizing agent, has been approved by a governmental regulatory authority, e.g., the United States Food and Drug Administration for any use. Any combination of antibody and associated target may be used in the methods of killing T lymphocytes provided herein.

In a specific embodiment, when the multimerizing agent or dimerizing agent is an antibody, said antibody is one that specifically binds to a CD20 epitope or mimotope, e.g., a human CD20 epitope or mimotope, and said extracellular domain of a cell death polypeptide comprises a CD20 epitope or mimotope to which said antibody specifically binds. In certain specific embodiments, when the multimerizing agent or dimerizing agent is an antibody, said antibody is rituximab and said extracellular domain of the cell death polypeptide comprises a CD20 epitope or a CD20 mimotope that binds to said rituximab; said antibody is tositumumab and said extracellular domain of the cell death polypeptide comprises a CD20 epitope or a CD20 mimotope that binds to said tositumumab; said antibody is ibritumomab and said extracellular domain of the cell death polypeptide comprises a CD20 epitope or a CD20 mimotope that binds said ibritumomab; said antibody is ofatumumab and said extracellular domain of the cell death polypeptide comprises a CD20 epitope or a CD20 mimotope that binds said ofatumumab; or said antibody is alemtuzumab and said extracellular domain of the cell death polypeptide comprises a CD52 epitope or a CD52 mimotope that binds to said alemtuzumab.

In certain specific embodiments, when the multimerizing agent or dimerizing agent is an antibody, said antibody is said antibody is basiliximab and said extracellular domain of the cell death polypeptide comprises a CD25 epitope or a CD25 mimotope that binds said basiliximab; said antibody is daclizumab and said extracellular domain of the cell death polypeptide comprises a CD25 epitope or a CD25 mimotope that binds said daclizumab; said antibody is brentuximab and said extracellular domain of the cell death polypeptide comprises a CD30 epitope or a CD30 mimotope that binds said brentuximab; said antibody is belimumab and said extracellular domain of the cell death polypeptide comprises a B-cell activating factor (BAFF) epitope or a BAFF mimotope that binds said belimumab; said antibody is cetuximab and said extracellular domain of the cell death polypeptide comprises an epidermal growth factor receptor (EGFR) epitope or an EGFR mimotope that binds said cetuximab; said antibody is panitumumab and said extracellular domain of the cell death polypeptide comprises an epidermal growth factor receptor (EGFR) epitope or an EGFR mimotope that binds said panitumumab; said antibody is efalizumab and said extracellular domain of the cell death polypeptide comprises an epitope of CD11a or a mimotope of CD11a that binds to said efalizumab; said antibody is ipilimumab and said extracellular domain of the cell death polypeptide comprises a CD152 epitope or CD152 mimotope that binds said ipilimumab; said antibody is natalizumab and said extracellular domain of the cell death polypeptide comprises an epitope of alpha-4 integrin or a mimotope of alpha 4 integrin that binds said natalizumab; or said antibody is basiliximab and said extracellular domain of the cell death polypeptide comprises a CD25 epitope or CD25 mimotope that binds said basiliximab.

In a specific embodiment of any of the above embodiments, when said antibody binds to said epitope or mimotope on at least two of said cell death polypeptides, the intracellular domains of said polypeptides, and/or the respective caspases in said intracellular domains multimerize or dimerize. In specific embodiments, when said antibody specifically binds to an epitope or mimotope of at least two cell death polypeptides, dimerization of the cell death polypeptides occurs, e.g., dimerization of the intracellular domains of the cell death polypeptides occurs. In particular embodiments the cell death polypeptides comprise intracellular domains comprising a caspase domain, and dimerization of the caspase domains occurs. In specific embodiments, said dimerization, for example, dimerization of intracellular domains, e.g., dimerization of caspase domains, initiates an apoptosis-inducing signal in said cell, e.g., T lymphocyte.

Without intending to be limited by theory, when the antibody binds to the respective epitopes or mimotopes on at least two of said polypeptides, the intracellular domains of said polypeptides multimerizes, e.g., dimerize, at which time the respective caspases in said intracellular domains dimerize. Dimerization of said polypeptides initiates an apoptosis-inducing signal in said T lymphocyte.

As above, receptors and their respective ligands may be used to multimerize or dimerize cell death polypeptides, and thereby effect killing of a cell, e.g., a T lymphocyte, comprising the polypeptide. For example, the extracellular domain of said cell death polypeptide is or comprises a receptor or a ligand-binding portion thereof. In such embodiments, the multimerizing agent or dimerizing agent comprises at least two ligands for said receptor or ligand binding portion thereof, enabling multimerization or dimerization of the cell death polypeptide when the multimerizing agent or dimerizing agent binds to said receptor or said ligand binding portion thereof on at least two of said polypeptides, said polypeptides are dimerized. In preferred embodiments, dimerization of said polypeptides initiates an apoptosis-inducing signal in said cell.

In other embodiments of the method of killing cells, e.g., T lymphocytes, the extracellular domain of the cell death polypeptide comprises a ligand for a receptor. In such embodiments of the method, the multimerizing agent or dimerizing agent comprises at least two receptors or ligand-binding portions thereof that bind to said ligand. When the multimerizing dimerizing agent binds to said receptor or said ligand binding portion thereof on two of said cell death polypeptides, the intracellular domains, and thus preferably the caspase domains, in said polypeptides are dimerized. Dimerization of said intracellular domains, and the caspase domains, preferably initiates an apoptosis-inducing signal is generated in said cell.

In certain other embodiments of the method of killing cells, e.g., T lymphocytes, said extracellular domain of said cell death polypeptide comprises an artificial oligonucleotide sequence. For example, in particular embodiments, said cell death polypeptide comprises an extracellular domain that comprises an artificial oligonucleotide sequence. In a specific embodiment, a multimerizing or dimerizing agent is or comprises at least one multimerizing or dimerizing oligonucleotide comprising a first oligonucleotide and a second oligonucleotide, optionally joined by a linker, wherein said first oligonucleotide and said second oligonucleotide are complementary to said artificial oligonucleotide sequence. In certain specific embodiments, said first oligonucleotide and said second oligonucleotide have the same sequence. In specific embodiments, said first oligonucleotide and said second oligonucleotide are joined in a head-to-head or tail-to-tail conformation. In specific embodiments, when said multimerizing or dimerizing oligonucleotide of said multimerizing agent or dimerizing agent hybridizes to the artificial oligonucleotide sequence of two of said cell death polypeptides, the cell death polypeptides are multimerized or dimerized. In another specific embodiment, when the cell death polypeptides are multimerized or dimerized, an apoptosis-inducing signal is generated in said cell. In particular embodiments, the cell death polypeptides comprise intracellular caspase domains, and when the intracellular caspase domains are multimerized or dimerized, an apoptosis-inducing signal is generated in said cell. In a specific embodiment, said cell is a T lymphocyte.

In certain other embodiments of the method of killing T lymphocytes, the multimerizing or dimerizing agent is an artificial polypeptide comprising two or more binding domains joined by one or more linkers.

In a specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said cell death polypeptide is dimerizable using an antibody, and wherein when said antibody dimerizes said polypeptide, an apoptosis-inducing signal is generated in said cell, comprising contacting said cell with an amount of said antibody sufficient to dimerize a sufficient number of said plurality of artificial polypeptides to dimerize and generate an aggregate apoptosis-inducing signal sufficient to kill said cell. In a specific embodiment, said cell is a T lymphocyte.

In another specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprises an extracellular domain comprising a receptor or ligand-binding portion thereof that bind a ligand, wherein said polypeptide is dimerizable using a dimerizing agent comprising two said ligands, and wherein when said dimerizing agent dimerizes two of said polypeptides, an apoptosis-inducing signal is generated in cell, comprising contacting said cell with an amount of said dimerizing agent sufficient to dimerize a sufficient number of said plurality of artificial cell death polypeptides to dimerize and generate an aggregate apoptosis-inducing signal sufficient to kill said cell. In a specific embodiment, said cell is a T lymphocyte.

In another specific embodiment, provided herein is a method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprises an extracellular domain comprising a ligand or receptor-binding portion thereof that bind a receptor or ligand-binding portion thereof, wherein said polypeptides are dimerizable using a dimerizing agent comprising two said receptors or ligand-binding portion thereof, and wherein when said dimerizing agent dimerizes two of said polypeptides, an apoptosis-inducing signal is generated in said cell, comprising contacting said cell with an amount of said dimerizing agent sufficient to dimerize a sufficient number of said plurality of artificial polypeptides to dimerize and generate an aggregate apoptosis-inducing signal sufficient to kill said cell. In a specific embodiment, said cell is a T lymphocyte.

In another specific embodiment, provided herein is method of killing a cell, e.g., a T lymphocyte, wherein said cell comprises a plurality of artificial cell death polypeptides each comprising a caspase or functional portion thereof, wherein said caspase is caspase 3, caspase 8 or caspase 9 (e.g., human caspase 3, caspase 8, or caspase 9), and, wherein said plurality of artificial polypeptides each comprising an extracellular domain comprising an artificial oligonucleotide, wherein said plurality of polypeptides are dimerizable using a dimerizing agent comprising an oligonucleotide comprising a first oligonucleotide and a second oligonucleotide, wherein said first oligonucleotide and said second oligonucleotide have the same nucleotide sequence, and wherein said first oligonucleotide and second oligonucleotide optionally are joined by a linker, and wherein said first oligonucleotide and said second oligonucleotide are complementary to said artificial oligonucleotide in said extracellular domain of said polypeptide, and wherein when said dimerizing agent dimerizes two of said cell death polypeptides, an apoptosis-inducing signal is generated in said cell, comprising contacting said cell with an amount of said dimerizing agent sufficient to dimerize a sufficient number of said plurality of artificial polypeptides to dimerize and generate an aggregate apoptosis-inducing signal sufficient to kill said cell. In a specific embodiment, said cell is a T lymphocyte.

In a specific embodiment, the T lymphocytes killed in accordance with the methods described herein are CAR-T lymphocytes.

4.3. Chimeric Antigen Receptors

When the cells provided herein are T lymphocytes which comprise the cell death polypeptides described above, such T lymphocytes can, in certain embodiments, comprise chimeric antigen receptors (CARs), which are artificial membrane-bound proteins that direct a T lymphocyte to an antigen, and stimulate the T lymphocyte to kill a cell displaying the antigen. See, e.g., Eshhar, U.S. Pat. No. 7,741,465. At a minimum, the CAR comprises an extracellular domain that binds to an antigen, e.g., an antigen on a cell, a transmembrane domain, and an intracellular (cytoplasmic) signaling domain that transmits a primary activation signal to an immune cell. All other conditions being satisfied, when the CAR is expressed on the surface of, e.g., a T lymphocyte, and the extracellular domain of the CAR binds to an antigen, the intracellular signaling domain transmits a signal to the T lymphocyte to activate and/or proliferate, and, if the antigen is present on a cell surface, to kill the cell expressing the antigen. Because T lymphocytes require two signals, a primary activation signal and a costimulatory signal, in order to activate, typically CARs also comprise a costimulatory domain such that binding of the antigen to the extracellular domain results in transmission of both a primary activation signal and a costimulatory signal.

4.3.1. General CAR Structure Intracellular Domain

In certain embodiments, the intracellular domain of the CAR is or comprises an intracellular domain or motif of a protein that is expressed on the surface of T lymphocytes and triggers activation and/or proliferation of said T lymphocytes. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fc receptor subunit or an IL-2 receptor subunit.

In certain embodiments, the CAR additionally comprises one or more co-stimulatory domains or motifs, e.g., as part of the intracellular domain of the polypeptide. The one or more co-stimulatory domains or motifs can be, or comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif.

The transmembrane region can be any transmembrane region that can be incorporated into a functional CAR, typically a transmembrane region from a CD4 or a CD8 molecule.

4.3.2. CAR Transmembrane Domains from CTLA4 or PD-1

In certain embodiments, the transmembrane domain of the CAR is from an immune system protein that normally transmits an inhibitory signal to such immune system cells, e.g., a transmembrane domain from CTLA4 (Cytotoxic T-Lymphocyte Antigen 4 or Cytotoxic T-Lymphocyte Associated protein 4) or PD-1 (Programmed Death-1).

In certain embodiments, any of the T lymphocytes provided herein, which comprise a plurality of cell death polypeptides, comprise a transmembrane domain from CTLA4 or PD-1 (Programmed Cell Death 1) In a specific embodiment, a T lymphocyte expressing said polypeptide, or any of such polypeptides described herein, is activated or stimulated to proliferate when said polypeptide binds to said antigen. In a specific embodiment, the polypeptide, when expressed on the surface of a T lymphocyte, directs the T lymphocyte to kill a cell expressing said antigen.

In specific embodiments of any of the polypeptides herein, in which the transmembrane domain of the polypeptide is from CTLA4, the CTLA4 transmembrane domain is from a mammalian CTLA4, e.g., human, primate, or rodent, e.g., murine CTLA4. Preferably, the transmembrane domain does not comprise amino acids from the intracellular domain, extracellular domain, or either intracellular or extracellular domain of CTLA4 or PD-1. Specific, non-limiting examples of CTLA4 or PD-1 transmembrane domain sequences are provided below.

In a specific embodiment, the CTLA4 transmembrane domain is the polypeptide sequence encoded by exon 3 of a human CTLA4 gene. In another specific embodiment, the CTLA4 transmembrane domain is or comprises the amino acid sequence PEPCPDSDFLLWILAAVSSGLFFYSFLL-TAVSLSKM (in three-letter code, Pro-Glu-Pro-Cys-Pro-Asp-Ser-Asp-Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val-Ser-Leu-Ser-Lys-Met) (SEQ ID NO:1). In another specific embodiment, the CTLA4 transmembrane domain is or comprises the polypeptide sequence encoded by nucleotides 610-722 of GenBank Accession No. NM_005214.4. In another specific embodiment, the CTLA4 transmembrane domain is or comprises the amino acid sequence PDSD-FLLWILAAVSSGLFFYSFLLTAVSL (in three-letter code, Pro-Asp-Ser-Asp-Phe-Leu-Leu-Trp-Ile-Leu-Ala-Ala-Val-Ser-Ser-Gly-Leu-Phe-Phe-Tyr-S er-Phe-Leu-Leu-Thr-Ala-V al-Ser-Leu) (SEQ ID NO:2). In another specific embodiment, the CTLA4 transmembrane domain is or comprises the polypeptide sequence encoded by nucleotides 636-699 of GenBank Accession No. NM 005214.4. In another specific embodiment, the CTLA4 transmembrane domain is or comprises the amino acid sequence FLLWI-LAAVSSGLFFYSFLLTAV (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val) (SEQ ID NO:3). See, e.g., Ensembl protein reference no. ENSP00000303939.3. In another specific embodiment, the CTLA4 transmembrane domain is or comprises the polypeptide sequence FLLWI-LAAVSSGLFFYSFLLT (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr) (SEQ ID NO:4), see, e.g., UNIPROT Accession No. P16410. In another specific embodiment, the CTLA4 transmembrane domain is or comprises the polypeptide sequence FLLWILVAVSLGLFFYSFLVSAVSLS (in three-letter code, Phe-Leu-Leu-Trp-Ile-Leu-Val-Ala-Val-Ser-Leu-Gly-Leu-Phe-Phe-Tyr-Ser-Phe-Leu-Val-Ser-Ala-Val-Ser-Leu-Ser) (SEQ ID NO:5). See, e.g., Shin et al., *Blood* 119:5678-5687 (2012). In another specific embodiment, the PD-1 transmembrane domain is or comprises the amino acid sequence TLVVGVVGGLLGSLVLLVWV-LAVICSRAA (in three-letter code, Thr-Leu-Val-Val-Gly-Val-Val-Gly-Gly-Leu-Leu-Gly-Ser-Leu-Val-Leu-Leu-Val-Trp-Val-Leu-Ala-Val-Ile-Cys-Ser-Arg-Ala-Ala) (SEQ ID NO:6). See Finger et al., *Gene* 197(1-2):177-187 (1997). In another specific embodiment, the PD-1 transmembrane domain is or comprises the amino acid sequence VGVVG-GLLGSLVLLVWVLAVI (in three-letter code, Val-Gly-Val-Val-Gly-Gly-Leu-Leu-Gly-Ser-Leu-Val-Leu-Leu-Val-Trp-Val-Leu-Ala-Val-Ile) (SEQ ID NO:7). See, e.g., UNIPROT Accession No. Q15116. In another specific embodiment, the PD-1 transmembrane domain is or comprises the amino acid sequence FQTLVVGVVGGLLGSLVLLVWVLAVI (in three-letter code, Phe-Glu-Thr-Leu-Val-Val-Gly-Val-Val-Gly-Gly-Leu-Leu-Gly-Ser-Leu-Val-Leu-Leu-Val-Trp-Val-Leu-Ala-Val-Ile) (SEQ ID NO:8). See, e.g., GenBank Accession No. NM 005018.2. In certain embodiments, a nucleotide sequence that encodes one of the transmembrane polypeptides disclosed herein comprises a nucleotide sequence that encodes any of the amino acid sequences disclosed in SEQ ID NO:1, SEQ ID NO:2, SEQ ID NO:3, SEQ ID NO:4, SEQ ID NO:5, SEQ ID NO:6, SEQ ID NO:7 or SEQ ID NO:8. In another specific embodiment, the PD-1 transmembrane domain is or comprises at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7 or SEQ ID NO:8. In certain embodiments, a nucleotide sequence that encodes one of the polypeptides disclosed herein comprises a nucleotide sequence that encodes at least 10, 11, 12, 13, 14, 15, 16, 17, 18, 19, 20 or 21 consecutive amino acids disclosed in SEQ ID NO:1, SEQ ID NO:2, SEQ ID NO:3, SEQ ID NO:4, SEQ ID NO:5, SEQ ID NO:6, SEQ ID NO:7 or SEQ ID NO:8. In constructing the polypeptide, e.g. CAR, in certain embodiments, human sequences may be combined with non human sequences. For example, a polypeptide, e.g. CAR comprising human extracellular and intracellular domain amino acid sequences may comprise a transmembrane domain from a non human species; e.g., may comprise a murine CTLA4 transmembrane domain or a murine PD-1 transmembrane domain. In a more specific embodiment, the polypeptide, e.g. CAR, comprises human amino acid sequences for the extracellular and intracellular domains, and comprises a transmembrane domain having, or consisting of, the amino acid sequence of SEQ ID NO:5.

4.3.3. CAR Intracellular Domain

The extracellular domain of the polypeptide binds to an antigen of interest. In certain embodiments of any of the polypeptides described herein, the extracellular domain comprises a receptor, or a portion of a receptor, that binds to said antigen. The extracellular domain may be, e.g., a receptor, or a portion of a receptor, that binds to said antigen. In certain embodiments, the extracellular domain comprises, or is, an antibody or an antigen-binding portion thereof. In specific embodiments, the extracellular domain comprises, or is, a single-chain Fv domain. The single-chain Fv domain can comprise, for example, a $V_L$ linked to $V_H$ by a flexible linker, wherein said $V_L$ and $V_H$ are from an antibody that binds said antigen.

The antigen to which the extracellular domain of the polypeptide binds can be any antigen of interest, e.g., can be an antigen on a tumor cell. The tumor cell may be, e.g., a cell in a solid tumor, or a cell of a blood cancer. The antigen can be any antigen that is expressed on a cell of any tumor or cancer type, e.g., cells of a lymphoma, a lung cancer, a breast cancer, a prostate cancer, an adrenocortical carcinoma, a thyroid carcinoma, a nasopharyngeal carcinoma, a melanoma, e.g., a malignant melanoma, a skin carcinoma, a colorectal carcinoma, a desmoid tumor, a desmoplastic small round cell tumor, an endocrine tumor, an Ewing sarcoma, a peripheral primitive neuroectodermal tumor, a solid germ cell tumor, a hepatoblastoma, a neuroblastoma, a non-rhabdomyosarcoma soft tissue sarcoma, an osteosarcoma, a retinoblastoma, a rhabdomyosarcoma, a Wilms tumor, a glioblastoma, a myxoma, a fibroma, a lipoma, or the like. In more specific embodiments, said lymphoma can be chronic lymphocytic leukemia (small lymphocytic lymphoma), B-cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma.

In a specific embodiment, in which the cancer is chronic lymphocytic leukemia (CLL), the B cells of the CLL have a normal karyotype. In other specific embodiments, in which the cancer is chronic lymphocytic leukemia (CLL), the B cells of the CLL carry a 17p deletion, an 11q deletion, a 12q trisomy, a 13q deletion or a p53 deletion.

In certain embodiments, the antigen is a tumor-associated antigen or a tumor-specific antigen. In various specific embodiments, without limitation, the tumor-associated antigen or tumor-specific antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MACE), CD19, CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein.

In certain embodiments, the TAA or TSA is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXB1, SPA17, SSX, SYCP1, or TPTE.

In certain other embodiments, the TAA or TSA is a carbohydrate or ganglioside, e.g., fuc-GM1, GM2 (oncofetal antigen-immunogenic-1; OFA-I-1); GD2 (OFA-I-2), GM3, GD3, and the like.

In certain other embodiments, the TAA or TSA is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML 1 fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, triosephosphate isomerase, Gage 3,4, 5,6,7, GnTV, Herv-K-mel, Lage-1, NA-88, NY-Eso-1/Lage-2, SP17, SSX-2, TRP2-Int2, gp100 (Pmel 17), tyrosinase, TRP-1, TRP-2, MAGE-1, MAGE-3, RAGE, GAGE-1, GAGE-2, p15(58), RAGE, SCP-1, Hom/Mel-40, PRAME, p53, H-Ras, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, CO-029, FGF-5, G250, Ga733 (EpCAM), HTgp-175, M344, MA-50, MG7-Ag, MOV18, NB\70K, NY-CO-1, RCAS1, SDCCAGI6, TA-90, TAAL6, TAG72, TLP, TPS, CD19, CD22, CD27, CD30, CD70, GD2 (ganglioside G2), EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), an abnormal ras protein, or an abnormal p53 protein. In another specific embodiment, said tumor-associated antigen or tumor-specific antigen is integrin αvβ3 (CD61), galactin, K-Ras (V-Ki-ras2 Kirsten rat sarcoma viral oncogene), or Ral-B. Other tumor-associated and tumor-specific antigens are known to those in the art.

Antibodies, and scFvs, that bind to TSAs and TAAs are known in the art, as are nucleotide sequences that encode them.

In certain specific embodiments, the antigen is an antigen not considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

In certain embodiments of the polypeptides described herein, the extracellular domain is joined to said transmembrane domain by a linker, spacer or hinge polypeptide sequence, e.g., a sequence from CD28 or a sequence from CTLA4.

4.3.4. Bispecific CARs

In certain embodiments of the T lymphocytes or methods described herein, the T lymphocytes, in addition to comprising a cell death polypeptide, comprise two or more CARs in which the primary signaling mechanism and costimulatory mechanism are split into two or more polypeptides.

In certain embodiments, for example, the T lymphocytes comprise a cell death polypeptide, and at least two different other polypeptides, e.g., chimeric receptors, in which the immune signal derived from binding of a primary signaling polypeptide, e.g., chimeric receptor, to a first antigen is separated from a costimulatory signal produced by a costimulatory polypeptide, e.g., chimeric receptor, wherein the costimulatory signal is dependent on antigen binding of a second antigen by the second chimeric receptor.

In one embodiment, the T lymphocyte comprises a primary signaling polypeptide comprising a first extracellular antigen binding domain that binds a first antigen, and a first intracellular signaling domain, wherein said primary signaling polypeptide does not comprise a co-stimulatory domain; and a co-stimulatory polypeptide comprising a second extracellular antigen binding domain binding a second antigen, or a receptor that binds said second antigen; and a second intracellular signaling domain; wherein said T lymphocyte becomes maximally cytotoxic only when said first signaling domain and said second signaling domain are both activated by said first antigen and said second antigen, respectively. In a specific embodiment, binding of said first antigen to said first antigen binding domain without binding of said second antigen to said second binding domain, or binding of said second antigen to said second antigen binding domain without binding of first second antigen to said first binding domain, induces anergy of said T lymphocyte, or non-responsiveness of said T-lymphocyte to said first antigen or said second antigen.

In another specific embodiment, said first antigen binding domain and said second antigen binding domain are independently an antigen-binding portion of a receptor, an antigen-binding portion of an antibody, or other peptide-based macromolecular antigen binding agent. In certain specific embodiments, either or both of said first antigen binding domain or said second antigen binding domain are scFv antibody fragments. In specific embodiments, either or both of said primary signaling polypeptide or said co-stimulatory polypeptide additionally comprise a transmembrane domain. In other specific embodiments, said primary signaling polypeptide or said co-stimulatory polypeptide comprises a T lymphocyte survival motif. In a specific embodiment, the T lymphocyte survival motif is a CD28 T lymphocyte survival motif. In other specific embodiments, said T lymphocyte survival motif is an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor ß (TGFß) receptor. In another more specific embodiment, said primary signaling polypeptide or said co-stimulatory polypeptide comprise a portion of a CD28 molecule that comprises a T lymphocyte survival motif. In a more specific embodiment, said primary signaling polypeptide or said co-stimulatory polypeptide comprise a CD28 molecule that comprises a T lymphocyte survival motif. In certain specific embodiments, said first intracellular signaling domain comprises a polypeptide sequence comprising an immunoreceptor tyrosine-based activation motif (ITAM). In a more specific embodiment, said polypeptide sequence is a CD3 signaling domain.

In certain specific embodiments, said first antigen is an antigen on a tumor cell. In a more specific embodiment, said tumor cell is a cell in a solid tumor. In another more specific embodiment, said tumor cell is a blood cancer cell. In another specific embodiment, said antigen is a tumor-associated antigen or a tumor-specific antigen. In more specific embodiments, said tumor-associated antigen or tumor-specific antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1, the dimeric form of the pyruvate kinase isoenzyme type M2 (tumor M2-PK), an abnormal ras protein, or an abnormal p53 protein.

In another specific embodiment, said second antigen is a growth factor, cytokine, or interleukin. The second antigen is a growth factor, cytokine, or interleukin associated with angiogenesis or vasculogenesis. In more specific embodiments, said second antigen is vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8).

In another specific embodiment, signal transduction activation provided by said second antigen is non-antigenic, but is associated with hypoxia. In more specific embodiments, said stimulus is induced by activation of hypoxia-inducible factor-1α (HIF-1α), HIF-1ß, HIF-2α, HIF-2ß, HIF-3α, or HIF-3ß.

In another specific embodiment, said second antigen is an interleukin.

In another specific embodiment, said second antigen is a damage associated molecular pattern molecule (DAMP; also known as an alarmin). In more specific embodiments, said DAMP is a heat shock protein, chromatin-associated protein high mobility group box 1 (HMGB1), S100A8 (also known as MRP8, or calgranulin A), S100A9 (also known as MRP14, or calgranulin B), serum amyloid A (SAA), deoxyribonucleic acid, adenosine triphosphate, uric acid, or heparin sulfate.

In certain specific embodiments, said second antigen is an antigen on an antibody that binds to an antigen presented by a tumor cell.

In a specific embodiment of any of the embodiments herein, said co-stimulatory polypeptide comprises one or more co-stimulatory domains. In specific embodiments, said one or more co-stimulatory domains comprises one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell co-stimulatory (ICOS) polypeptide sequence.

In a specific embodiment, said primary signaling polypeptide comprises an extracellular tumor antigen-binding domain and a CD3ζ signaling domain, and wherein said co-stimulatory polypeptide comprises an antigen-binding domain wherein said antigen is an angiogenic or vasculogenic factor, and one or more co-stimulatory molecule signaling domains. Said angiogenic factor can be, e.g., VEGF. Said one or more co-stimulatory molecule signaling motifs can comprise, e.g., co-stimulatory signaling domains from each of CD28, OX40, and 4-1BB. In a more specific embodiment, said primary signaling polypeptide comprises an extracellular tumor antigen-binding domain and a CD3c signaling domain, and wherein said co-stimulatory polypeptide comprises an antigen-binding domain wherein said antigen is VEGF, and co-stimulatory signaling domains from each of CD28, OX40, and 4-1BB.

In a more specific embodiment, said primary signaling polypeptide or said co-stimulatory polypeptide comprises a T lymphocyte survival motif. In more specific embodiments, said T lymphocyte survival motif is, or is derived from, an intracellular signaling domain of IL-7 receptor (IL-7R), an intracellular signaling domain of IL-12 receptor, an intracellular signaling domain of TL-15 receptor, an intracellular signaling domain of IL-21 receptor, or an intracellular signaling domain of transforming growth factor ß (TGFß) receptor. In a more specific embodiment of said T lymphocyte, therefore, said primary signaling polypeptide comprises an extracellular tumor antigen-binding domain and a CD3ζ signaling domain, and wherein said co-stimulatory polypeptide comprises an antigen-binding domain wherein said antigen is VEGF, an IL-7 receptor intracellular T lymphocyte survival motif, and co-stimulatory signaling domains from each of CD28, OX40, and 4-1BB.

In another specific embodiment of the T lymphocyte, said first antigen is a tumor-specific antigen or a tumor-associated antigen, and said first intracellular signaling domain comprises a CD3c signaling domain; and wherein said costimulatory polypeptide comprises an antigen-binding domain that binds said second antigen, and co-stimulatory signaling domains from each of CD28, OX40, and 4-1BB. In a more specific embodiment, said co-stimulatory polypeptide further comprises an intracellular T lymphocyte survival motif, e.g., a T lymphocyte survival motif that is, or is derived from, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor ß (TGFß) receptor.

In a specific embodiment of any of the T lymphocytes provided herein, said second antigen is VEGF or IL-4.

In another aspect, provided herein is a T lymphocyte comprising a cell death polypeptide, a co-stimulatory polypeptide comprising a first extracellular antigen binding domain that binds a first antigen, and a first intracellular signaling domain; and a primary signaling polypeptide comprising a second extracellular antigen binding domain binding a second antigen, or a receptor that binds said second antigen; and a second intracellular signaling domain, wherein said primary signaling polypeptide does not comprise a co-stimulatory domain; wherein said modified lymphocyte becomes maximally cytotoxic only when said first signaling domain and said second signaling domain are both activated by said first antigen and said second antigen, respectively. In a specific embodiment, binding of said first antigen to said first antigen binding domain without binding of said second antigen to said second binding domain, or binding of said second antigen to said second antigen binding domain without binding of first second antigen to said first binding domain induces anergy of said T lymphocyte, or non-responsiveness of said T lymphocyte to said first antigen. In a specific embodiment, said first antigen-binding domain and said antigen-binding domain are independently an antigen-binding portion of a receptor or an antigen-binding portion of an antibody. In another specific embodiment, either or both of said first antigen binding domain or said second antigen binding domain are scFv antibody fragments. In specific embodiments, said co-stimulatory polypeptide and/or said primary signaling polypeptide additionally comprise a transmembrane domain. In a more specific embodiment, said co-stimulatory polypeptide or said primary signaling polypeptide comprises a T lymphocyte survival motif, e.g., any of the T lymphocyte survival motifs described herein. In another specific embodiment, said first antigen is an antigen on a tumor cell, e.g., a cell in a solid tumor or a blood cancer cell. In a specific embodiment, said first antigen is a tumor-associated antigen or a tumor-specific antigen, e.g., Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1, the dimeric form of the pyruvate kinase isoenzyme type M2 (tumor M2-PK), an abnormal ras protein, an abnormal p53 protein, CD19, CD22, CD27, CD30, CD70, GD2 (ganglioside G2), EGFRvIII (epidermal growth factor variant III), sperm protein 17 (Sp17), mesothelin, PAP (prostatic acid phosphatase), protein, TARP (T cell receptor gamma alternate reading frame protein), Trp-p8, or STEAP1 (six-transmembrane epithelial antigen of the prostate 1). In another specific embodiment, said tumor-associated antigen or tumor-specific antigen is integrin αvβ3 (CD61), galactin, K-Ras (V-Ki-ras2 Kirsten rat sarcoma viral oncogene), or Ral-B.

In certain specific embodiments, said second intracellular signaling domain comprises a polypeptide sequence comprising an immunoreceptor tyrosine-based activation motif (ITAM), e.g., a CD3ζ signaling domain. In a specific embodiment, said second antigen is a growth factor, cytokine, or interleukin. In another specific embodiment, said second antigen is a growth factor, cytokine, or interleukin associated with angiogenesis or vasculogenesis, e.g., VEGF, bFGF, PDGF, HGF, IGF, or IL-8. In other more specific embodiments, signal transduction by said second chimeric receptor is induced by activation of a hypoxia-associated factor, e.g., HIF-1α, HIF-1β, HIF-2α, HIF-2β, HIF-3α, or HIF-3β. In other specific embodiments, said second antigen is an interleukin. In other specific embodiments, said second antigen is a DAMP, e.g., a heat shock protein, HMGB1, S100A8, S100A9, SAA, DNA, ATP, uric acid, or heparin sulfate. In other specific embodiments, said second antigen is an administered peptide, e.g., an antibody or a synthetic polypeptide. In other specific embodiments, said second antigen is an antigen on an antibody that binds to an antigen presented by a tumor cell. In certain specific embodiments, said co-stimulatory polypeptide comprises one or more co-stimulatory domains, e.g., one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell co-stimulatory (ICOS) polypeptide sequence. In any of the above embodiments, in a specific embodiment, said co-stimulatory polypeptide or said primary signaling polypeptide comprises a T lymphocyte survival motif, e.g., said T lymphocyte survival motif is, or is derived from, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor ß (TGFß) receptor.

4.4. Isolated Polypeptides

Any of the polypeptides, comprising a CTLA4 or PD-1 transmembrane domain, provided herein, may be modified by, e.g., acylation, amidation, glycosylation, methylation, phosphorylation, sulfation, sumoylation, ubiquitylation, or the like. The polypeptides may be labeled with a label capable of providing a detectable signal, e.g., with radio-isotopes and fluorescent compounds. One or more side chains of the first or second polypeptides may be derivatized, e.g., derivatization of lysinyl and amino terminal residues with succinic or other carboxylic acid anhydrides, or derivatization with, e.g., imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-azonia-4,4-dimethylpentyl)carbodiimide.

4.5. Isolated Nucleic Acids

The polypeptides provided herein (e.g., chimeric receptors) can be encoded by polynucleotide sequences according to well-known methods in the art. The polynucleotides may be contained within any polynucleotide vector suitable for the transformation of immune cells, e.g., T lymphocytes. For example, T lymphocytes may be transformed using synthetic vectors, lentiviral or retroviral vectors, autonomously replicating plasmids, a virus (e.g., a retrovirus, lentivirus, adenovirus, or herpes virus), or the like, containing polynucleotides encoding the first and second polypeptides (e.g., chimeric receptors). Lentiviral vectors suitable for transformation of T lymphocytes include, but are not limited to, e.g., the lentiviral vectors described in U.S. Pat. Nos. 5,994,136; 6,165,782; 6,428,953; 7,083,981; and 7,250,299, the disclosures of which are hereby incorporated by reference in their entireties. HIV vectors suitable for transformation of T lymphocytes include, but are not limited to, e.g., the vectors described in U.S. Pat. No. 5,665,577, the disclosure of which is hereby incorporated by reference in its entirety.

Nucleic acids useful in the production of the first and second polypeptides, e.g., within a T lymphocyte, include DNA, RNA, or nucleic acid analogs. Nucleic acid analogs can be modified at the base moiety, sugar moiety, or phosphate backbone, and can include deoxyuridine substitution for deoxythymidine, 5-methyl-2'-deoxycytidine or 5-bromo-2'-deoxycytidine substitution for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chain. 4:5-23. In addition, the deoxyphosphate backbone can be replaced with, for example, a phosphorothioate or phosphorodithioate backbone, a phosphoroamidite, or an alkyl phosphotriester backbone.

4.6. Cells

Non-limiting examples of cells in which the cell death polypeptides and multimerizing or dimerizing agents may be used include, but are not limited to, natural killer (NK) cells, dendritic cells (DC), placental stem cells (e.g., the placental stem cells disclosed in U.S. Pat. Nos. 7,468,276; 8,057,788 and 8,202,703, the disclosures of which are hereby incorporated by reference in their entireties), mesenchymal-like stem cells from umbilical cord blood, placental blood, peripheral blood, bone marrow, dental pulp, adipose tissue, osteochondral tissue, and the like; embryonic stem cells, embryonic germ cells, neural crest stem cells, neural stem cells, and differentiated cells (e.g., fibroblasts, etc.). The cell death polypeptides, and multimerizing or dimerizing agents, may also be used in tumor cell lines, e.g., for animal model experimental purposes.

In a specific embodiment, the cells comprising the polypeptides provided herein are T lymphocytes. The T lymphocytes comprising the polypeptides provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T lymphocytes have been isolated from, or are expanded from T lymphocytes expanded from, peripheral blood, cord blood, or lymph.

The immune cells, e.g., T lymphocytes, used in the present methods are preferably autologous to an individual to whom the T lymphocytes are to be administered. In certain other embodiments, the T lymphocytes are allogeneic to an individual to whom the T lymphocytes are to be administered. Where allogeneic T lymphocytes are used to prepare T lymphocytes, it is preferable to select T lymphocytes that will reduce the possibility of graft-versus-host disease (GVHD) in the individual. For example, in certain embodiments, virus-specific T lymphocytes are selected for preparation of T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

In one embodiment, T lymphocytes are obtained from an individual, optionally then expanded, and then transformed with a polynucleotide encoding a cell death polypeptide, and optionally one or more polynucleotides encoding one or more CAR(s), and optionally then expanded. In another embodiment, T lymphocytes are obtained from an individual, optionally then expanded, and then transformed with a polynucleotide encoding a cell death polypeptide, and optionally one or more polynucleotides encoding one or more CAR(s), and optionally then expanding. Cells containing any of the polynucleotide may be selected using one or more selectable markers.

In certain embodiments, any of the T lymphocytes provided herein express or comprise native TCR proteins, e.g., TCR-α and TCR-β that are capable of forming native TCR complexes, in addition to the CTLA4 or PD-1 transmembrane domain-containing polypeptide. In certain other embodiments, either or both of the native genes encoding TCR-α and TCR-β in the T lymphocytes are modified to be non-functional, e.g., a portion or all are deleted, a mutation is inserted, etc.

In certain embodiments, any of the T lymphocytes provided herein are isolated from a tumor lesion, e.g., are tumor-infiltrating lymphocytes; such T lymphocytes are expected to be specific for a TSA or TAA.

T lymphocytes, and T lymphocytes comprising a polypeptide comprising a CD3c signaling domain and a CD28 co-stimulatory domain can be expanded using antibodies to CD3 and CD28, e.g., antibodies attached to beads, or to the surface of a cell culture plate; see, e.g., U.S. Pat. Nos. 5,948,893; 6,534,055; 6,352,694; 6,692,964; 6,887,466; and 6,905,681.

In any of the above embodiments, the antigen and/or antibody can exist free in the medium in which the T lymphocytes are cultures, or either or both can be attached to a solid support, e.g., tissue culture plastic surface, beads, or the like.

The T lymphocytes provided herein can optionally comprise a second type of "suicide gene" or "safety switch", in addition to the cell death polypeptide. For example, the T lymphocytes, in certain embodiments, can comprise an HSV thymidine kinase gene (HSV-TK), which causes death of the T lymphocytes upon contact with gancyclovir. In another embodiment, the T lymphocytes express or comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., *Blood* 105(11):4247-4254 (2005).

4.7. Methods of Using Cells Comprising Cell Death Polypeptides

The cells, e.g., T lymphocytes, provided herein that comprise cell death polypeptides and optionally one or more CARs, as described elsewhere herein, can be used to treat an individual having one or more types of cells desired to be targeted by the cells described herein, e.g., one or more types of cells to be killed. In certain embodiments, the cells to be killed are cancer cells, e.g., tumor cells. In specific embodiments, the cancer cells are cells of a solid tumor. In specific embodiments, the cells are cells of a lymphoma, a lung cancer, a breast cancer, a prostate cancer, an adrenocortical carcinoma, a thyroid carcinoma, a nasopharyngeal carcinoma, a melanoma, e.g., a malignant melanoma, a skin carcinoma, a colorectal carcinoma, a desmoid tumor, a desmoplastic small round cell tumor, an endocrine tumor, an Ewing sarcoma, a peripheral primitive neuroectodermal tumor, a solid germ cell tumor, a hepatoblastoma, a neuroblastoma, a non-rhabdomyosarcoma soft tissue sarcoma, an osteosarcoma, a retinoblastoma, a rhabdomyosarcoma, a Wilms tumor, a glioblastoma, a myxoma, a fibroma, a lipoma, or the like. In more specific embodiments, said lymphoma can be chronic lymphocytic leukemia (small lymphocytic lymphoma), B-cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma.

In certain embodiments, when the modified cells, e.g., modified T lymphocytes described herein are administered to a subject in need thereof, the combination of multimerizing agent and cell death polypeptide selected are chosen such that they are compatible with the patient population (or subpopulation) in which the cells, e.g., T lymphocytes, have been administered. By way of example only, if the multimerizing agent selected is the antibody rituximab, then in certain embodiments the patient population is individuals having a cancer of the B cells, e.g., B cell lymphoma.

Efficacy of the cells, e.g., T lymphocytes, after administration to an individual having a disease or disorder remediable by such cells, e.g., T lymphocytes, e.g., an individual having cancer, can be assessed by one or more criteria, specific to the particular disease or disorder, known to those of ordinary skill in the art, to be indicative of progress of the disease or disorder. Generally, administration of the cells to such an individual is effective when one or more of said criteria detectably, e.g., significantly, moves from a disease state value or range to, or towards, a normal value or range.

The cells, e.g., T lymphocytes, may be formulated in any pharmaceutically-acceptable solution, preferably a solution suitable for the delivery of living cells, e.g., saline solution (such as Ringer's solution), gelatins, carbohydrates (e.g., lactose, amylose, starch, or the like), fatty acid esters, hydroxymethylcellulose, polyvinyl pyrolidine, etc. Such preparations are preferably sterilized prior to addition of the cells, and may be mixed with auxiliary agents such as lubricants, preservatives, stabilizers, emulsifiers, salts for influencing osmotic pressure, buffers, and coloring. Pharmaceutical carriers suitable for use in formulating the cells are known in the art and are described, for example, in WO 96/05309.

In certain embodiments, the cells, e.g., T lymphocytes, are formulated into individual doses, wherein said individual doses comprise at least, at most, or about $1\times10^4$, $5\times10^4$, $1\times10^5$, $5\times10^5$, $1\times10$ $5\times10^6$, $1\times10^7$, $5\times10^7$, $1\times10^8$, $5\times10^8$, $1\times10^9$, $5\times10^9$, $1\times10^{10}$, $5\times10^{10}$, or $1\times10^{11}$ T lymphocytes. In certain embodiments, the cells are formulated for intravenous, intraarterial, parenteral, intramuscular, subcutaneous, intrathecal, or intraocular administration, or administration within a particular organ or tissue.

5. EXAMPLES

5.1. Example 1: Treatment of B Cell Lymphoma

An individual presents with B-cell chronic lymphocytic leukemia, a B cell lymphoma. Testing of B cells from the individual determines that the B cells carry a 17p deletion. T lymphocytes are obtained from the individual, transfected with a lentiviral vector comprising a nucleotide sequence that encodes a chimeric antigen receptor (CAR), and transfected with a second lentiviral vector comprising a nucleotide sequence encoding a dimerizable cell death polypeptide comprising an extracellular domain that comprises a mimotope that can be bound by the antibody rituximab, and an intracellular domain that comprises a caspase 9 domain. The T lymphocytes are expanded using CD3+CD28-coated beads to sufficient numbers for administration. The chimeric receptor comprises an extracellular antigen-binding region that binds to CD19; a transmembrane domain from CTLA4; intracellular co-stimulatory domain from CD28; and an intracellular CD3ζ domain. The individual is administered between $10^9$ and $10^{10}$ of the T lymphocytes in 200 mL saline solution by intravenous infusion over 30 minutes. The individual is monitored for two weeks afterwards to establish a reduction of at least 90% of CD19+ B cells in the individual's blood. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m² or until symptoms abate.

5.2. Example 2: Treatment of a B Cell Lymphoma

An individual presents with B-cell chronic lymphocytic leukemia, a B cell lymphoma. Testing of B cells from the individual determines that the B cells carry a 17p deletion.

About $10^6$ T lymphocytes are obtained from the individual, transfected with a lentiviral vector comprising a nucleotide sequence encoding a cell death polypeptide comprising an extracellular domain that comprises a mimotope that can be bound by the antibody rituximab and an intracellular domain that comprises a caspase 8 domain, and transfected with a lentiviral vector comprising a nucleotide sequence that encodes a CAR. The CAR comprises an extracellular antigen-binding region that binds to CD19; a transmembrane domain from PD-1; intracellular co-stimulatory domain from CD28; and an intracellular CD3 domain. CAR-expressing T lymphocytes are administered to the individual without prior expansion of the T lymphocytes. The individual is administered between $10^5$ and $10^6$ of the T lymphocytes in 200 mL saline solution by intravenous infusion over 30 minutes. The individual is monitored for two weeks afterwards to establish a reduction of at least 90% of CD19+ B cells in the individual's blood. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.3. Example 3: Treatment of B Cell Lymphoma

An individual presents with B-cell chronic lymphocytic leukemia, a B cell lymphoma. Testing of B cells from the individual determines that the B cells carry a p53 deletion. T lymphocytes are obtained from the individual, transfected with a lentiviral vector comprising a nucleotide sequence encoding a cell death polypeptide comprising an extracellular domain that comprises an epitope that can be bound by the antibody rituximab and an intracellular domain that comprises a caspase 3 domain, and transfected with a lentiviral vector comprising a nucleotide sequence that encodes a CAR. The T lymphocytes are expanded using CD3+CD28-coated beads to sufficient numbers for administration. The CAR comprises an extracellular antigen-binding region that binds to CD19; a transmembrane domain from CTLA4; intracellular co-stimulatory domains from each of CD28, 4-1BB, and OX40; and an intracellular CD3c domain. The individual is administered between $10^9$ and $10^{10}$ of the T lymphocytes in 200 mL saline solution by intravenous infusion over 30 minutes. The individual is monitored for two weeks afterwards to establish a reduction of at least 90% of CD19+ B cells in the individual's blood. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.4. Example 4: Treatment of a B Cell Lymphoma

An individual presents with B-cell chronic lymphocytic leukemia, a B cell lymphoma. Testing of B cells from the individual determines that the B cells carry a p53 deletion. About $10^6$ T lymphocytes are obtained from the individual, transfected with a lentiviral vector comprising a nucleotide sequence encoding a cell death polypeptide comprising an extracellular domain that comprises an epitope that can be bound by the antibody rituximab and an intracellular domain that comprises a caspase 9 domain, and transfected with a lentiviral vector comprising a nucleotide sequence that encodes a CAR. The CAR comprises an extracellular antigen-binding region that binds to CD19; a transmembrane domain from PD-1; intracellular co-stimulatory domains from each of CD28, 4-1BB, and OX40; and an intracellular CD3c domain. CAR-expressing T lymphocytes are administered to the individual without prior expansion of the T lymphocytes. The individual is administered between $10^5$ and $10^6$ of the T lymphocytes in 200 mL saline solution by intravenous infusion over 30 minutes. The individual is monitored for two weeks afterwards to establish a reduction of at least 90% of CD19+ B cells in the individual's blood. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.5. Example 5: Treatment of Prostate Cancer

An individual presents with stage T2 prostate cancer, with no spread to regional or other lymph nodes (N0, M0). Histological grade is determined to be G2. Overall, the individual is determined to have Stage II prostate cancer. The individual is administered between $10^9$ and $10^{10}$ T lymphocytes that comprise a CAR, in 200 mL saline solution by intravenous infusion over 30 minutes. The CAR comprises an extracellular antigen-binding region that binds to PSCA, a transmembrane domain from CTLA4, intracellular co-stimulatory domain from CD28, and an intracellular CD3ζ domain. The T lymphocytes also comprise a cell death polypeptide comprising an extracellular domain that comprises an epitope that can be bound by the antibody rituximab, and an intracellular domain that comprises a caspase 3, caspase 8, or caspase 9 domain. The individual is re-assessed for prostate cancer stage and spread to lymph nodes, and histology of biopsied prostate tissue is performed, at 30, 60 and 90 days post-administration. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.6. Example 6: Treatment of Prostate Cancer

An individual presents with stage T2 prostate cancer, with no spread to regional or other lymph nodes (N0, M0). Histological grade is determined to be G2. Overall, the individual is determined to have Stage II prostate cancer. The individual is administered between $10^9$ and $10^{10}$ T lymphocytes that comprise a CAR, in 200 mL saline solution by intravenous infusion over 30 minutes. The CAR comprises an extracellular antigen-binding region that binds to PSCA, a transmembrane domain from PD-1, intracellular co-stimulatory domain from CD28, and an intracellular CD3ζ domain. The T lymphocytes also comprise a cell death polypeptide comprising an extracellular domain that comprises an epitope that can be bound by the antibody rituximab, and an intracellular domain that comprises a caspase 3, caspase 8, or caspase 9 domain. The individual is re-assessed for prostate cancer stage and spread to lymph nodes, and histology of biopsied prostate tissue is performed, at 30, 60 and 90 days post-administration. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.7. Example 7: Treatment of Prostate Cancer

An individual presents with stage T2 prostate cancer, with no spread to regional or other lymph nodes (N0, M0). Histological grade is determined to be G2. Overall, the individual is determined to have Stage II prostate cancer. The individual is administered between $10^9$ and $10^{10}$ T lymphocytes that comprise a CAR, in 200 mL saline solution by intravenous infusion over 30 minutes. The CAR comprises an extracellular antigen-binding region that binds to PSCA, a transmembrane domain from CTLA-4, intracellular co-stimulatory domains from each of CD28, 4-1BB, and OX40, and an intracellular CD3ζ domain. The T lymphocytes also comprise a cell death polypeptide comprising an extracellular domain that comprises an epitope that can be bound by the antibody rituximab, and an intracellular domain that comprises a caspase 3, caspase 8, or caspase 9 domain. The individual is re-assessed for prostate cancer stage and spread to lymph nodes, and histology of biopsied prostate tissue is performed, at 30, 60 and 90 days post-administration. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

5.8. Example 8: Treatment of Prostate Cancer

An individual presents with stage T2 prostate cancer, with no spread to regional or other lymph nodes (N0, M0). Histological grade is determined to be G2. Overall, the individual is determined to have Stage II prostate cancer. The individual is administered between $10^9$ and $10^{10}$ T lymphocytes that comprise a CAR, in 200 mL saline solution by intravenous infusion over 30 minutes. The CAR comprises an extracellular antigen-binding region that binds to PSCA, a transmembrane domain from PD-1, intracellular co-stimulatory domains from each of CD28, 4-1BB, and OX40, and an intracellular CD3ζ domain. The T lymphocytes also comprise a cell death polypeptide comprising an extracellular domain that comprises an epitope that can be bound by the antibody rituximab, and an intracellular domain that comprises a caspase 3, caspase 8, or caspase 9 domain. The individual is re-assessed for prostate cancer stage and spread to lymph nodes, and histology of biopsied prostate tissue is performed, at 30, 60 and 90 days post-administration. Where the patient, after administration of the T lymphocytes, shows signs of distress due to the T lymphocytes (e.g., difficulty breathing, fever, abnormal serum cytokine levels, rash, or the like), rituximab is administered at a dosage of 200-500 mg/m$^2$ or until symptoms abate.

EQUIVALENTS

The present disclosure is not to be limited in scope by the specific embodiments described herein. Indeed, various modifications of the subject matter provided herein, in addition to those described, will become apparent to those skilled in the art from the foregoing description. Such modifications are intended to fall within the scope of the appended claims.

Various publications, patents and patent applications are cited herein, the disclosures of which are incorporated by reference in their entireties.

What is claimed:

1. A T lymphocyte comprising an artificial cell death polypeptide, wherein said artificial cell death polypeptide is a transmembrane protein comprising an extracellular domain that comprises a CD52 epitope or mimotope, a transmembrane domain, and an intracellular domain comprising an apoptosis-inducing domain, wherein said apoptosis-inducing domain is caspase 3, caspase 8 or caspase 9, wherein said artificial cell death polypeptide is dimerizable using an anti-CD52 antibody that binds to said CD52 epitope or mimotope, and wherein when said antibody dimerizes said artificial cell death polypeptide, an apoptosis-inducing signal is generated in said T lymphocyte.

2. The T lymphocyte of claim 1, wherein said antibody has been approved by the United States Food and Drug Administration for any use.

3. The T lymphocyte of claim 1, wherein said antibody is alemtuzumab.

4. The T lymphocyte of claim 3, wherein said extracellular domain comprises a CD52 epitope.

5. The T lymphocyte of claim 3, which further comprises a chimeric antigen receptor (CAR) that recognizes an antigen on a tumor cell.

6. The T lymphocyte of claim 5, wherein said antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, or the dimeric form of the pyruvate kinase isoenzyme type M2 (tumor M2-PK).

7. The T lymphocyte of claim 1, which further comprises a chimeric antigen receptor (CAR) that recognizes an antigen on a tumor cell.

8. The T lymphocyte of claim 7, wherein said tumor cell is a cell in a solid tumor.

9. The T lymphocyte of claim 7, wherein said tumor cell is a cell of a blood cancer.

10. The T lymphocyte of claim 7, wherein said antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, or the dimeric form of the pyruvate kinase isoenzyme type M2 (tumor M2-PK).

11. A method of killing a T lymphocyte, wherein said T lymphocyte comprises a plurality of artificial cell death polypeptides, wherein each of said artificial cell death polypeptides is a transmembrane protein comprising an extracellular domain that comprises a CD52 epitope or mimotope, a transmembrane domain, and an intracellular domain comprising an apoptosis-inducing domain, wherein said apoptosis-inducing domain is caspase 3, caspase 8 or caspase 9, wherein each of said artificial cell death polypeptides is dimerizable using an anti-CD52 antibody that binds to said CD52 epitope or mimotope, and wherein when said antibody dimerizes said artificial cell death polypeptides, an apoptosis-inducing signal is generated in said T lymphocyte,
   comprising contacting said T lymphocyte with an amount of said antibody sufficient for said plurality of artificial cell death polypeptides to dimerize and generate an aggregate apoptosis-inducing signal sufficient to kill said T lymphocyte.

12. The method of claim 11, wherein said antibody has been approved by the United States Food and Drug Administration for any use.

13. The method of claim 11, wherein said antibody is alemtuzumab.

14. The method of claim 13, wherein said extracellular domain comprises a CD52 epitope.

15. The method of claim 11, wherein said T lymphocyte further comprises a chimeric antigen receptor (CAR) that recognizes an antigen on a tumor cell.

16. The method of claim 15, wherein said antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, or the dimeric form of the pyruvate kinase isoenzyme type M2 (tumor M2-PK).

17. The method of claim 13, wherein said T lymphocyte further comprises a chimeric antigen receptor (CAR) that recognizes an antigen on a tumor cell.

18. The method of claim 17, wherein said antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, or the dimeric form of the pyruvate kinase isoenzyme type M2 (tumor M2-PK).

19. The method of claim 11, wherein the method is for killing the T lymphocyte in an individual to whom the T lymphocyte has been administered, wherein the contacting of said T lymphocyte with an amount of said antibody comprises administering the amount of said antibody to the individual, and wherein the method is for use in the event that the administration of the T lymphocyte causes any unwanted or deleterious effects in the patient receiving the T lymphocyte or in the event that the presence of the T lymphocyte in the patient is no longer necessary.

20. The method of claim 13, wherein the method is for killing the T lymphocyte in an individual to whom the T lymphocyte has been administered, wherein the contacting of said T lymphocyte with an amount of said antibody comprises administering the amount of said antibody to the individual, and wherein the method is for use in the event that the administration of the T lymphocyte causes any unwanted or deleterious effects in the patient receiving the T lymphocyte or in the event that the presence of the T lymphocyte in the patient is no longer necessary.

* * * * *

```
                       SEQUENCE LISTING

<160> NUMBER OF SEQ ID NOS: 8

<210> SEQ ID NO 1
<211> LENGTH: 36
<212> TYPE: PRT
<213> ORGANISM: Homo sapiens
<220> FEATURE:
<223> OTHER INFORMATION: sequence of CTLA4 transmembrane domain

<400> SEQUENCE: 1

Pro Glu Pro Cys Pro Asp Ser Asp Phe Leu Leu Trp Ile Leu Ala Ala
1               5                   10                  15

Val Ser Ser Gly Leu Phe Phe Tyr Ser Phe Leu Leu Thr Ala Val Ser
            20                  25                  30

Leu Ser Lys Met
        35

<210> SEQ ID NO 2
<211> LENGTH: 29
<212> TYPE: PRT
<213> ORGANISM: Homo sapiens
<220> FEATURE:
<223> OTHER INFORMATION: sequence of CTLA4 transmembrane domain

<400> SEQUENCE: 2

Pro Asp Ser Asp Phe Leu Leu Trp Ile Leu Ala Ala Val Ser Ser Gly
1               5                   10                  15

Leu Phe Phe Tyr Ser Phe Leu Leu Thr Ala Val Ser Leu
            20                  25
```

```
<210> SEQ ID NO 3
<211> LENGTH: 23
<212> TYPE: PRT
<213> ORGANISM: Homo sapiens
<220> FEATURE:
<223> OTHER INFORMATION: sequence of CTLA4 transmembrane domain

<400> SEQUENCE: 3

Phe Leu Leu Trp Ile Leu Ala Ala Val Ser Ser Gly Leu Phe Phe Tyr
1               5                   10                  15

Ser Phe Leu Leu Thr Ala Val
            20

<210> SEQ ID NO 4
<211> LENGTH: 21
<212> TYPE: PRT
<213> ORGANISM: Homo sapiens
<220> FEATURE:
<223> OTHER INFORMATION: sequence of CTLA4 transmembrane domain

<400> SEQUENCE: 4

Phe Leu Leu Trp Ile Leu Ala Ala Val Ser Ser Gly Leu Phe Phe Tyr
1               5                   10                  15

Ser Phe Leu Leu Thr
            20

<210> SEQ ID NO 5
<211> LENGTH: 26
<212> TYPE: PRT
<213> ORGANISM: Artificial Sequence
<220> FEATURE:
<223> OTHER INFORMATION: sequence of CTLA4 transmembrane domain

<400> SEQUENCE: 5

Phe Leu Leu Trp Ile Leu Val Ala Val Ser Leu Gly Leu Phe Phe Tyr
1               5                   10                  15

Ser Phe Leu Val Ser Ala Val Ser Leu Ser
            20                  25

<210> SEQ ID NO 6
<211> LENGTH: 29
<212> TYPE: PRT
<213> ORGANISM: Artificial Sequence
<220> FEATURE:
<223> OTHER INFORMATION: sequence of PD-1 transmembrane domain

<400> SEQUENCE: 6

Thr Leu Val Val Gly Val Val Gly Gly Leu Leu Gly Ser Leu Val Leu
1               5                   10                  15

Leu Val Trp Val Leu Ala Val Ile Cys Ser Arg Ala Ala
            20                  25

<210> SEQ ID NO 7
<211> LENGTH: 21
<212> TYPE: PRT
<213> ORGANISM: Homo sapiens
<220> FEATURE:
<223> OTHER INFORMATION: sequence of PD-1 transmembrane domain

<400> SEQUENCE: 7

Val Gly Val Val Gly Gly Leu Leu Gly Ser Leu Val Leu Leu Val Trp
1               5                   10                  15

Val Leu Ala Val Ile
            20
```

```
<210> SEQ ID NO 8
<211> LENGTH: 26
<212> TYPE: PRT
<213> ORGANISM: Unknown
<220> FEATURE:
<223> OTHER INFORMATION: sequence of PD-1 transmembrane domain

<400> SEQUENCE: 8

Phe Gln Thr Leu Val Val Gly Val Val Gly Gly Leu Leu Gly Ser Leu
1               5                   10                  15

Val Leu Leu Val Trp Val Leu Ala Val Ile
            20                  25
```